US006643546B2

(12) United States Patent
Mathis et al.

(10) Patent No.: US 6,643,546 B2
(45) Date of Patent: Nov. 4, 2003

(54) MULTI-ELECTRODE APPARATUS AND METHOD FOR TREATMENT OF CONGESTIVE HEART FAILURE

(75) Inventors: Scott Mathis, Durango, CO (US); John K. Prentice, Durango, CO (US); John A. Schmidt, Durango, CO (US); William B. Rottenberg, Durango, CO (US)

(73) Assignee: Quetzal Biomedical, Inc., Denver, CO (US)

(*) Notice: Subject to any disclaimer, the term of this patent is extended or adjusted under 35 U.S.C. 154(b) by 0 days.

(21) Appl. No.: 10/075,808

(22) Filed: Feb. 13, 2002

(65) Prior Publication Data

US 2002/0169484 A1 Nov. 14, 2002

Related U.S. Application Data

(60) Provisional application No. 60/268,449, filed on Feb. 13, 2001.

(51) Int. Cl.[7] ................................................. A61N 1/18
(52) U.S. Cl. ........................... 607/9; 607/123; 607/148
(58) Field of Search ............................ 607/9, 119, 123, 607/148

(56) References Cited

U.S. PATENT DOCUMENTS

| 4,686,987 A | 8/1987 | Salo et al. ............ 128/419 PG |
| 4,702,253 A | 10/1987 | Nappholz et al. ..... 128/419 PG |
| 4,730,619 A | 3/1988 | Koning et al. ........ 128/419 PG |
| 4,773,401 A | 9/1988 | Citak et al. ........... 128/419 PG |
| 4,865,036 A | 9/1989 | Chirife .................. 128/419 D |
| 4,901,725 A | 2/1990 | Nappholz et al. ..... 128/419 PG |
| 5,036,849 A | 8/1991 | Huack et al. ......... 128/419 PG |
| 5,074,303 A | 12/1991 | Huack .................. 128/419 PG |
| 5,137,019 A | 8/1992 | Pederson et al. ..... 128/419 PG |
| 5,154,171 A | 10/1992 | Chirife ................. 128/419 PG |
| 5,179,949 A | 1/1993 | Chirife ................. 128/419 PG |
| 5,190,035 A | 3/1993 | Salo et al. ............ 128/419 PG |
| 5,197,467 A | 3/1993 | Steinhaus et al. ..... 128/419 PG |
| 5,201,808 A | 4/1993 | Steinhaus et al. ..... 128/419 PG |
| 5,284,136 A | 2/1994 | Hauck et al. .................. 607/24 |
| 5,309,917 A | 5/1994 | Wang et al. ................ 128/696 |
| 5,361,776 A | 11/1994 | Samuelson et al. ......... 128/734 |
| 5,391,190 A | 2/1995 | Pederson et al. ............. 607/23 |
| 5,417,717 A | 5/1995 | Salo et al. ..................... 607/18 |
| 5,800,465 A | * 9/1998 | Thompson et al. ............ 607/9 |

* cited by examiner

*Primary Examiner*—Mark Bockelman
(74) *Attorney, Agent, or Firm*—Gottlieb, Rackman & Reisman, P.C.; John R. Merkling

(57) ABSTRACT

An apparatus and method for treatment of congestive heart failure from the right side of the heart. An implantable cardiac stimulation system with a multi-electrode lead having three or more selectable electrodes, together with apparatus for identifying an optimal subset of electrodes, apparatus for shaping a propagating wave front, and apparatus for modifying the intrinsic ventricular cardiac activation sequence, or generating simultaneous or near simultaneous pacing pulses to the septum or right ventricular outflow tract during ventricular systole in order to improve left ventricular cardiac efficiency and reduce mitral regurgitation in patients with dilated cardiomyopathy. A three dimensional map of electrode placement may be calculated. A sub set of the available electrodes in the right side of the heart is selected for stimulation such that septal motion during systole is reduced or the mitral valve area is stiffened to reduce mitral regurgitation.

32 Claims, 17 Drawing Sheets

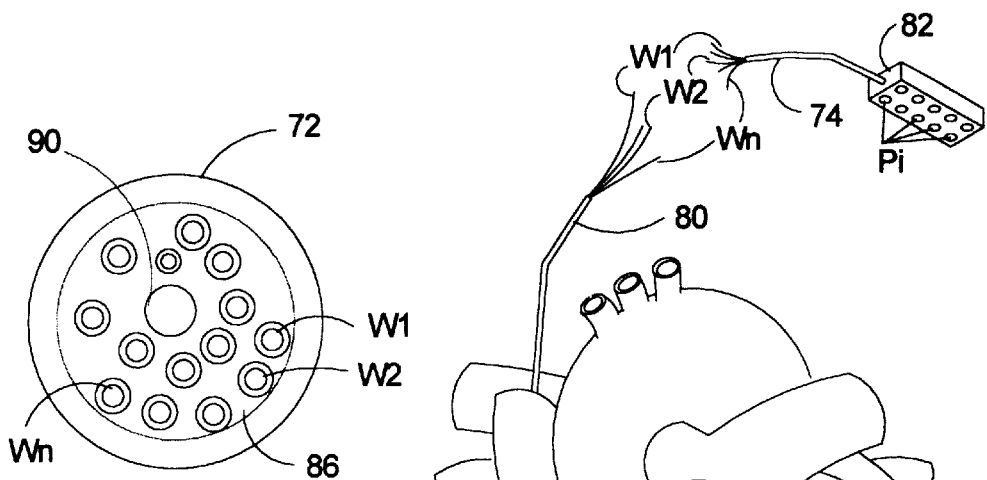
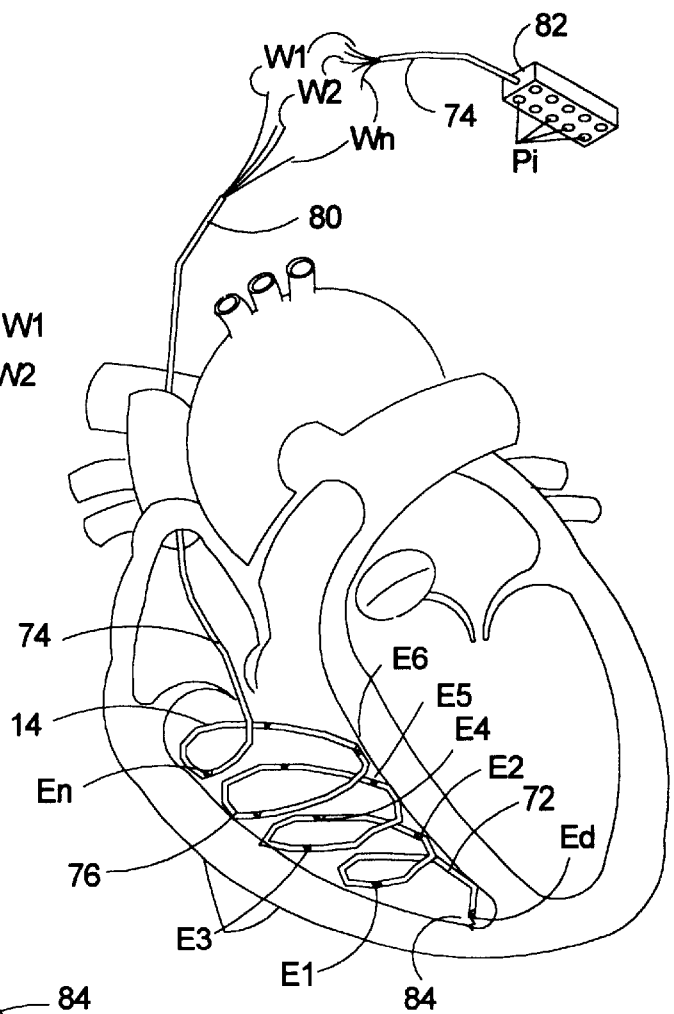
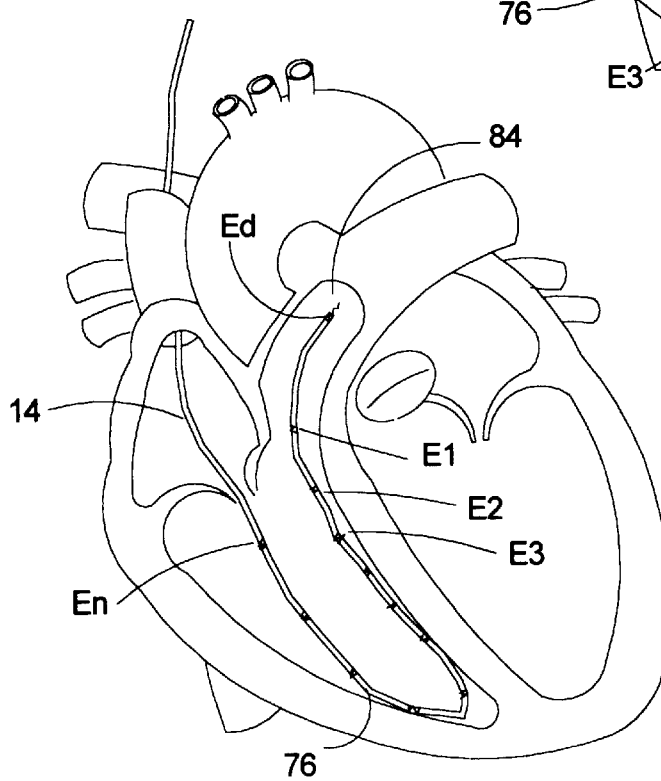
Fig. 12
Fig. 8
Fig. 9

MULTI-ELECTRODE APPARATUS AND METHOD FOR TREATMENT OF CONGESTIVE HEART FAILURE

This application claims the benefit of Provisional Application No. 60/268,449, filed Feb. 13, 2001.

BACKGROUND OF THE INVENTION

A. Field of Invention

This invention pertains to a method and apparatus for applying cardiac stimulation using multiple electrodes, and more particularly, to a method and apparatus for treatment of congestive heart failure.

B. Description of the Prior Art

The heart is a mechanical pump that is stimulated by electrical impulses. The mechanical action of the heart results in the flow of blood. During a normal heartbeat, the right atrium (RA) fills with blood from the returning veins. The RA then contracts and this blood is moved into the right ventricle (RV). When the RV contracts it pumps that blood to the lungs. Blood returning from the lungs moves into the left atrium (LA), and after LA contraction, is pumped into the left ventricle (LV), which then pumps it throughout the body. Four heart valves keep the blood flowing in the proper directions.

The electrical signal that drives this mechanical contraction starts in the sino-atrial node, a collection of specialized heart cells in the right atrium that automatically depolarize (change their voltage potential). This depolarization wave front passes across all the cells of both atria and results in atrial contraction. When the advancing wave front reaches the A-V node it is delayed so that the contracting atria have time to fill the ventricles. The depolarizing wave front then passes over the ventricles, causing them to contract and pump blood to the lungs and body. This electrical activity occurs approximately 72 times a minute in a normal individual and is called normal sinus rhythm.

The corresponding electrical signals identifying these events are usually referred to as the P, QRS (or R) and T waves or beats. More particularly, an atrial contraction is represented on an ECG by a P wave, a ventricular contraction is represented by an R wave and a ventricular repolarization is represented by a T wave. The atrium also repolarizes but this event (the U wave) is masked by activity in the ventricle and consequently it is not observable on an ECG.

Congestive heart failure is a condition that causes many deaths annually. The condition is characterized by weakness, breathlessness, abdominal discomfort, edema in the lungs and the lower portions of the body resulting from venous statis and reduced outflow of blood. These symptoms are associated with the inability of the heart to pump sufficient blood. Insufficiency may be associated with either the left ventricle, the right ventricle, or both. Cardiac output insufficiency may be caused by the failure of the heart to contract in an efficient way. If the physiologic conduction system has broken down, the chambers of the heart may not contract in a coordinated or effective manner. It is believed that cardiac efficiency could be improved by cardiac pacing that commences at or near physiologically optimum locations, or that can control or modify a cardiac wave front as the wave front passes through a chamber of the heart. In addition, dilated cardiomyopathy associated with heart failure often leads to a dysynchrony between the contraction of the left and right ventricles and to mitral regurgitation. Ventricular dysynchrony results in paradoxical septal wall motion and in reduction of cardiac output. Mitral regurgitation also results in a reduction in cardiac output. Both conditions increase myocardial strain that in turn leads to progression of the dilated cardiomyopathy via the expression of myocardial stretch proteins. Reduction in myocardial strain is thought to result in down regulation of these stretch proteins and a consequent slowing of the progression of or reversal of the dilated cardiomyopathy via reverse myocardial remodeling. Cardiac pacing to resynchronize ventricular contractions has been shown to increase cardiac output and reduce myocardial wall strain and it has been observed to produce reverse cardiac remodeling in human clinical studies. It is believed that cardiac pacing to directly control the contraction of the septal wall could also increase output, reduce mitral regurgitation, and reduce myocardial strain, leading to increased cardiac efficiency and potentially reverse remodeling. Cardiac pacing to modify the left ventricular base-to-apex activation sequence could also reduce mitral regurgitation, and again produce increased cardiac efficiency and potentially reverse remodeling.

Conventional pacemakers utilize a single or dual leads to apply pacing pulses. The dual (bipolar) lead typically includes a tip and a ring electrode. The lead is inserted in such a manner that the tip is imbedded into the cardiac muscle. A pacing pulse is then applied between the tip and the ring electrodes, thereby causing the cardiac muscle to contract. If a single unipolar electrode lead is used, the electric pulse is applied between the tip electrode and another electrode outside the heart, for example, the housing of the pacemaker. Bradycardia pacing therapy has usually been delivered through a pacing electrode implanted near the ventricular apex, that is, near the bottom of the heart. This location has been preferred not for physiologic reasons, but because most lead designs favor implantation at this site. A lead entering the right ventricle from the right atrium tends to extend into the lower apex of the ventricle where an active fixation apparatus, such as a helical corkscrew, may be used to secure the lead to the heart wall. Even if the distal tip of the lead is implanted at another location, it may be difficult or impossible to move the electrode to another location within the heart after initial implantation. The physician is thus limited to a single site for applying treatment. Bradycardia pacing therapy can be improved by delivering the stimulating pulse to a more efficient location than the ventricular apex. Studies have indicated that the abnormal contraction that results from apical pacing has long-term deleterious effects. Short-term studies using conventional pacing leads implanted in alternative locations have shown clinical improvements, but the long-term reliability of conventional pacing leads in these alternative locations is questionable and lead placement is difficult.

A single stimulating electrode, such as one available on a conventional lead, may not be implanted close enough to a physiologically preferred location in the patient's heart to cause improved cardiac efficiency when the pacemaker stimulates the heart. In fact, stimulating at the bottom end of the ventricle may diminish cardiac efficiency as compared to a wave propagated from the top of the ventricle. Moreover, an apparatus with a single electrode cannot control cardiac contraction, guide the propagation of a wave front, force a selected path for a stimulating wave front, or create a coordinated simultaneous or near simultaneous cardiac contraction of large sections of the myocardium. Such controlled contractions may result in more efficient cardiac contraction, thereby reducing the overall demand on the heart, allowing the body to alleviate the symptoms associated with inefficient blood flow.

OBJECTIVES AND SUMMARY OF THE INVENTION

In view of the above disadvantages of the prior art, it is an objective of the present invention to provide an implantable cardiac stimulation system, such as a pacemaker, in which three or more electrodes are positioned in a chamber of the heart and an optimum electrode or electrodes are selected for pacing.

A further objective is to provide an implantable cardiac stimulation system with apparatus for shaping or modifying a propagating wave front, modifying the intrinsic ventricular cardiac activation sequence, or generating simultaneous or near simultaneous pacing pulses to the septum or right ventricular outflow tract during ventricular systole in order to improve left ventricular cardiac efficiency and reduce mitral regurgitation in patients with dilated cardiomyopathy.

Another object of the invention is to provide a cardiac stimulator system that uses multiple electrodes that can pace simultaneously or sequentially through any or all of the electrodes.

Other objectives and advantages of the invention shall become apparent from the following description.

Briefly, the subject invention pertains to an implantable cardiac stimulation system having a cardiac stimulator having electronic circuitry for the stimulation and a multi-electrode lead attached to the stimulator and inserted into one or more body cavities. (The term cardiac stimulator will be used herein to cover pacemakers as well as other cardiac devices such as internal cardioversion devices and defibrillators.) The lead is inserted into the cardiac cavity into a predetermined position. Alternatively the lead may be positioned in the veins, or it may be positioned externally of the heart. Since the lead has many electrodes, then an appropriate subset of electrodes is selected for stimulation.

More specifically, an implantable cardiac stimulation system is disclosed with a stimulator adapted to sense intrinsic cardiac activity and to generate a stimulation pulse or pulses responsive to intrinsic cardiac activity, said stimulation pulse or pulses having an amplitude associated with a stimulation threshold; and a plurality of implanted electrodes including at least one optimum electrode selected based on a physiologic parameter related to cardiac efficiency. Stimulation of the heart for a selected chamber usually begins at the optimum electrode or electrodes. Additional electrodes are implanted in a patient's heart. These electrodes may be along a wave front propagation path, such that a wave front may be modified or reshaped by additional stimulation at selected electrodes, they may be at sites to be stimulated simultaneously or nearly simultaneously to cause a regional contraction of portions of the ventricular septum, or they may be positioned to induce a specific left ventricular activation sequence. Means are provided to identify the optimum electrode or set of electrodes and to identify the pattern in which cardiac tissue should be stimulated by the additional electrodes. Such means may involve stimulating pulses. A three dimensional map of electrode placement may be calculated. The relative locations of the electrodes may be determined by sensing an artificial wave front, emanating from a known electrode, such as the distal tip electrode or by field mapping techniques involving high frequency signals.

In a preferred embodiment, a lead having an elongated member is provided with the electrodes being formed on said elongated member. The electrodes comprise axially spaced electrodes disposed on said elongated member, each electrode being connected by a wire extending though said elongated member. The electrodes may be circumferential coils integral or continuous with the wires or may be rings connected to the wires by crimping or laser welding, for example. An electrode may also be provided at the distal end of the lead. The elongated member may be a tube housing the wires. The electrodes can be angularly spaced with respect to each about the elongated member. The tube may include an elongated cavity adapted to receive a removable stylet. The stylet may be more rigid then the lead and may be used for the implantation of the lead. After the lead is implanted, the stylet is removed.

In another aspect of the invention, a method is presented for treating congestive heart failure by implanting a lead having at least three electrodes, identifying an optimum electrode or electrodes for stimulation based on cardiac efficiency, and stimulating the heart through the optimum electrode or electrodes.

BRIEF DESCRIPTION OF THE DRAWINGS

FIG. 8 is a view of a multi-electrode lead implanted in a heart.

FIG. 9 is a view of a second configuration of the multi-electrode lead in the heart.

FIG. 12 is a cross section of the multi-electrode lead of FIG. 8.

DETAILED DESCRIPTION OF THE INVENTION

Figure 1:
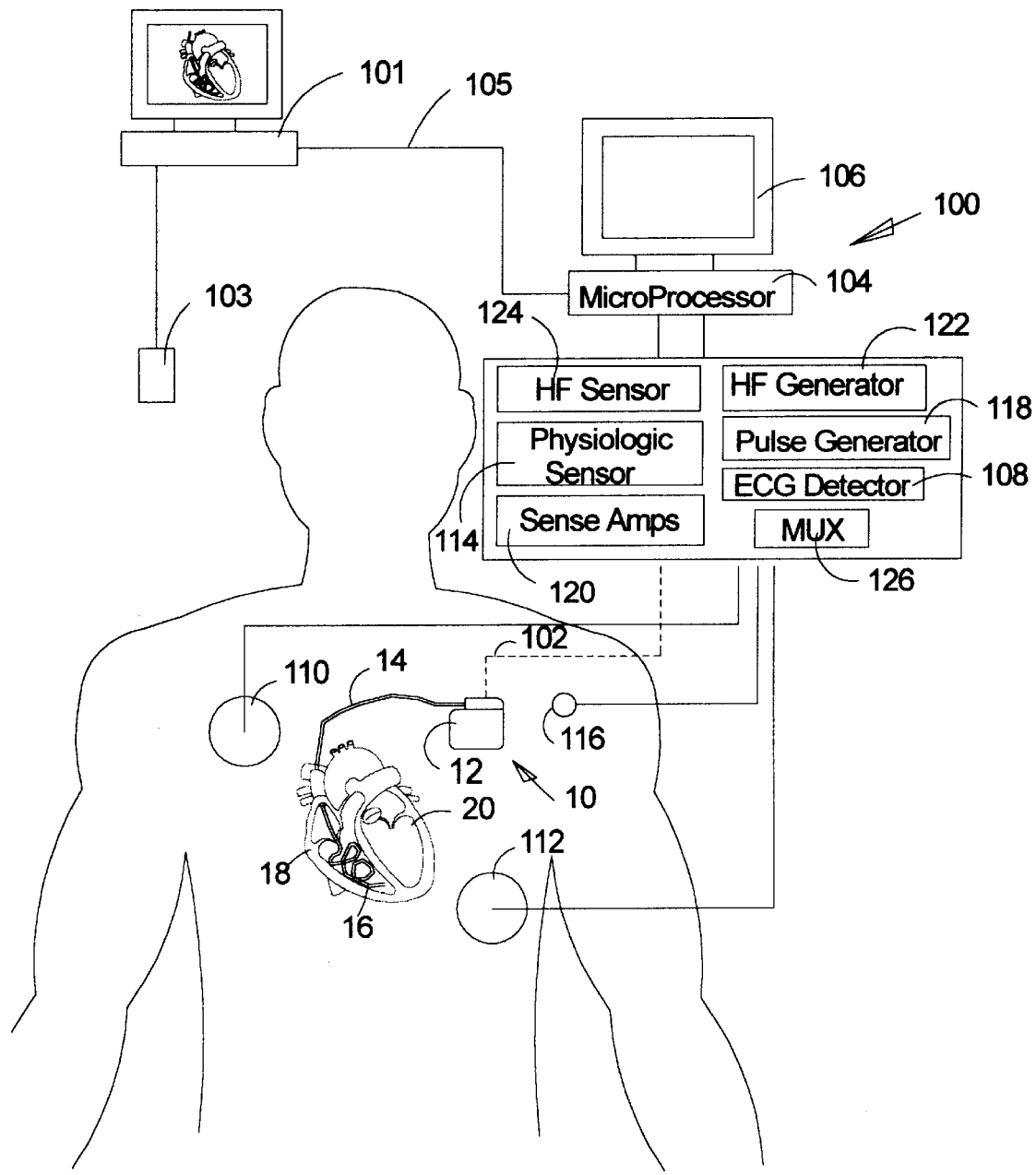
FIG. 1 shows a diagrammatic front view of a patient with a cardiac stimulation system, including a programmer used to program the cardiac stimulator.

The subject invention pertains to an implantable cardiac stimulation system 10 including a cardiac stimulator 12 with various electronic circuits, and a multi-electrode lead 14 attached to the stimulator 12, as shown. The lead 14 has a distal end 16 disposed, for example, in one of the cardiac chambers such as the right ventricle 18 of heart 20. In FIG. 1, end 16 is shown having a general spiral shape. The system 10 is adapted to deliver therapy in the form of electrical pulses. The therapy may include GCV (greater cardiac vein) resynchronization therapy, treatment of conduction pathway abnormalities, bardycardia pacing, etc. The cardiac stimulator 12 contains electronic components common to current cardiac stimulators such as a battery, microprocessor control circuit, ROM, RAM, an oscillator, reed switch and antenna for communication, output circuits, and sense circuits. These components are well known to those of skill in the art. In addition the cardiac stimulator 12 has a plurality of independent sensing and stimulating circuits for each heart chamber, as will be explained below.

Cardiac Stimulator

Figure 2:
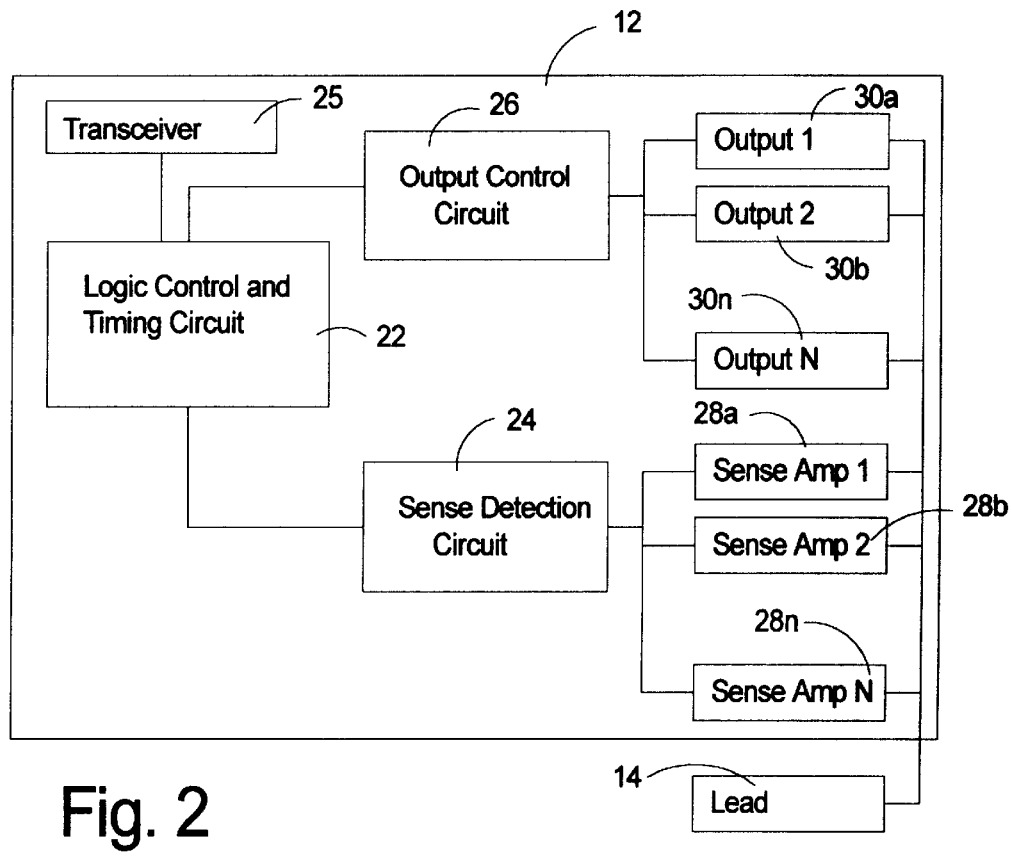
FIG. 2 shows a block diagram of the cardiac stimulator or FIG. 1.

FIG. 2 illustrates important elements of the cardiac stimulator 12 in block diagram. The cardiac stimulator 12 comprises a logic control and timing circuit 22, which may include a microprocessor and memory, but which could also be implemented in a specialized circuit. The logic control and timing circuit 22 receives input from a sense detection circuit 24 and issues control instructions to an output control circuit 26. To accommodate the many electrodes used in the apparatus, multiple sense amplifiers 28a, 28b . . . 28n are provided, each in electrical communication with an electrode through the lead 14 and with the sense detection circuit 24. Similarly, the output control circuit 26 is electrically connected to a plurality of output circuits 30a, 30b . . . 30n. The output circuits 30a, 30b . . . 30n produce stimulating pulses or high frequency, non-simulating signals at electrodes in the heart through the lead 14. The logic control and timing circuit 22 may operate in accordance with a program stored into memory. The programming in memory is received through a transceiver 25 (for instance from programmer 100). As part of this programming, the electrodes designated for stimulation, as described below, are stored in memory. During its operation, the microprocessor of the logic control and timing circuit 22 sets the output control circuit 26 and the sense detection circuit 24 in accordance with the appropriate electrode designations. Thereafter, the sensing detection circuit 24 senses intrinsic activity and other signals within the heart 20 and provides corresponding indication signals to the microprocessor. The Logic control and timing circuit 22 then issues appropriate commands to the output control circuit 26. The output control circuit 26 generates appropriate stimulation pulses. These pulses are steered to the designated electrode or electrodes.

Output Circuits

Figure 3:
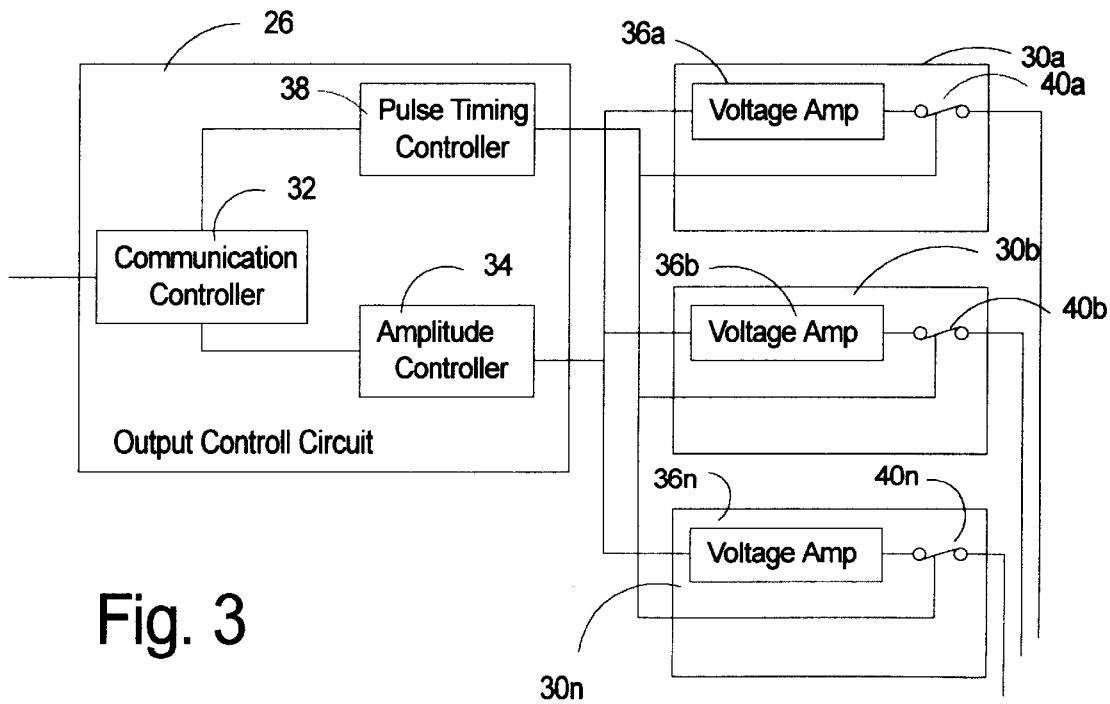
FIG. 3 is a block diagram of a portion of the circuits of FIG. 2.
Figure 4:
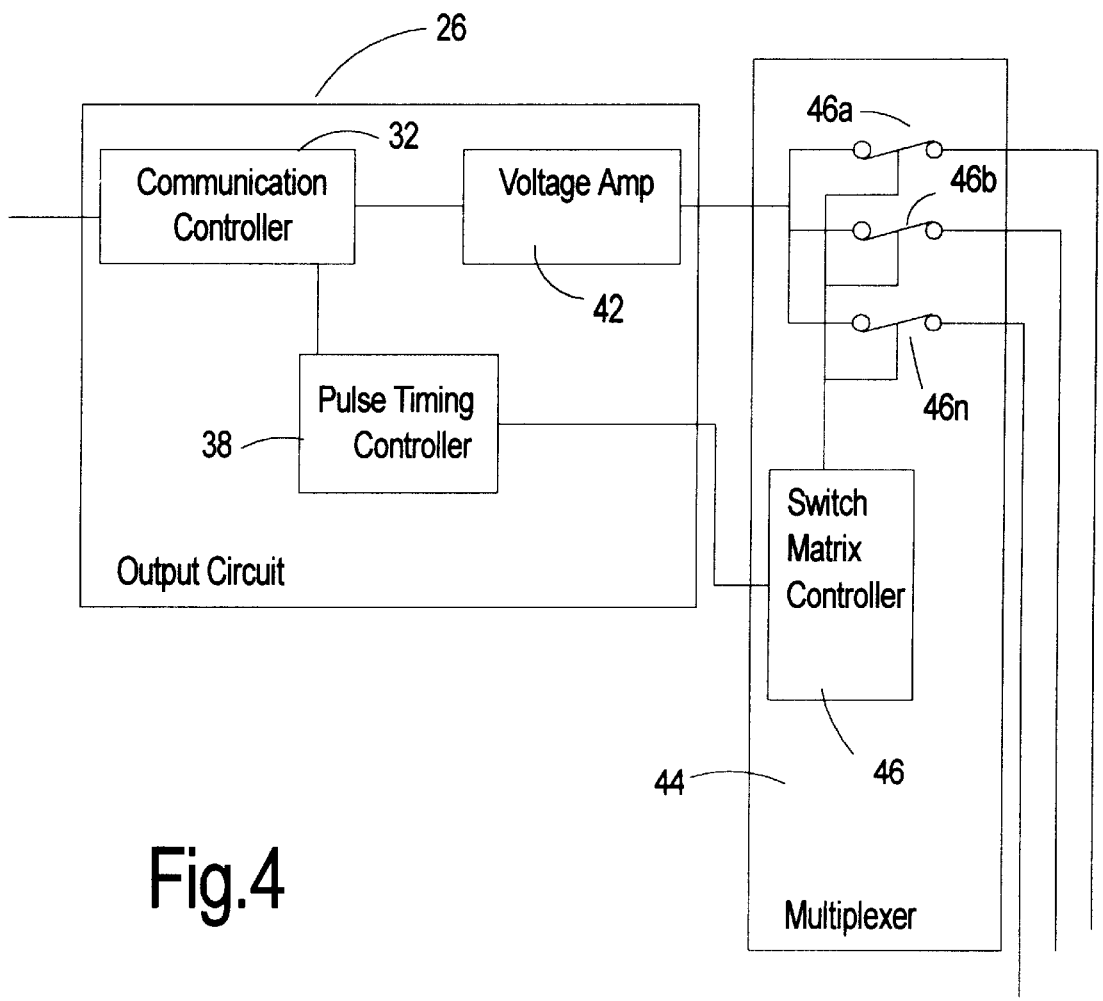
FIG. 4 is a second embodiment of the circuit portion of FIG. 3.

FIGS. 3 and 4 show two embodiments of output control circuits 26 and output circuits 30a, 30b . . . 30n. The embodiment of FIG. 3 comprises a communications controller that receives control signals from the logic control and timing circuit 22 (FIG. 2). Output of the communications controller 32 is sent to an amplitude controller 34 that controls the voltages produced by a plurality of voltage amplifiers 36a, 36b . . . 36n. In parallel, the communications controller 32 also regulates a pulse timing controller 38. Signals from the pulse timing controller 38 close and open switches 40a, 40b . . . 40n, thereby delivering stimulation pulses or high frequency signals to the heart through electrodes on the lead 14. The embodiment of FIG. 4 also uses a communication controller 32 and pulse timing controller 38, but the amplitude controller 34 and plurality of voltage amplifiers 36a, 36b . . . 36n are replaced by a single voltage amplifier 42. To achieve the same effect of multiple pulses to selected electrodes, the signals from the pulse timing controller are sent to a multiplexer 44, comprising a switch matrix controller 46 and a plurality of switches 48a, 48b . . . 48n. The switches 48a, 48b . . . 48n must be opened and closed in a synchronized manner. It may be necessary to open all switches before and after closing a selected switch. Thus the embodiment of FIG. 4 gains simplicity and energy efficiency by minimizing the number of voltage amplifiers, but sacrifices flexibility in potential output patterns.

Sense Circuits

Figure 5:
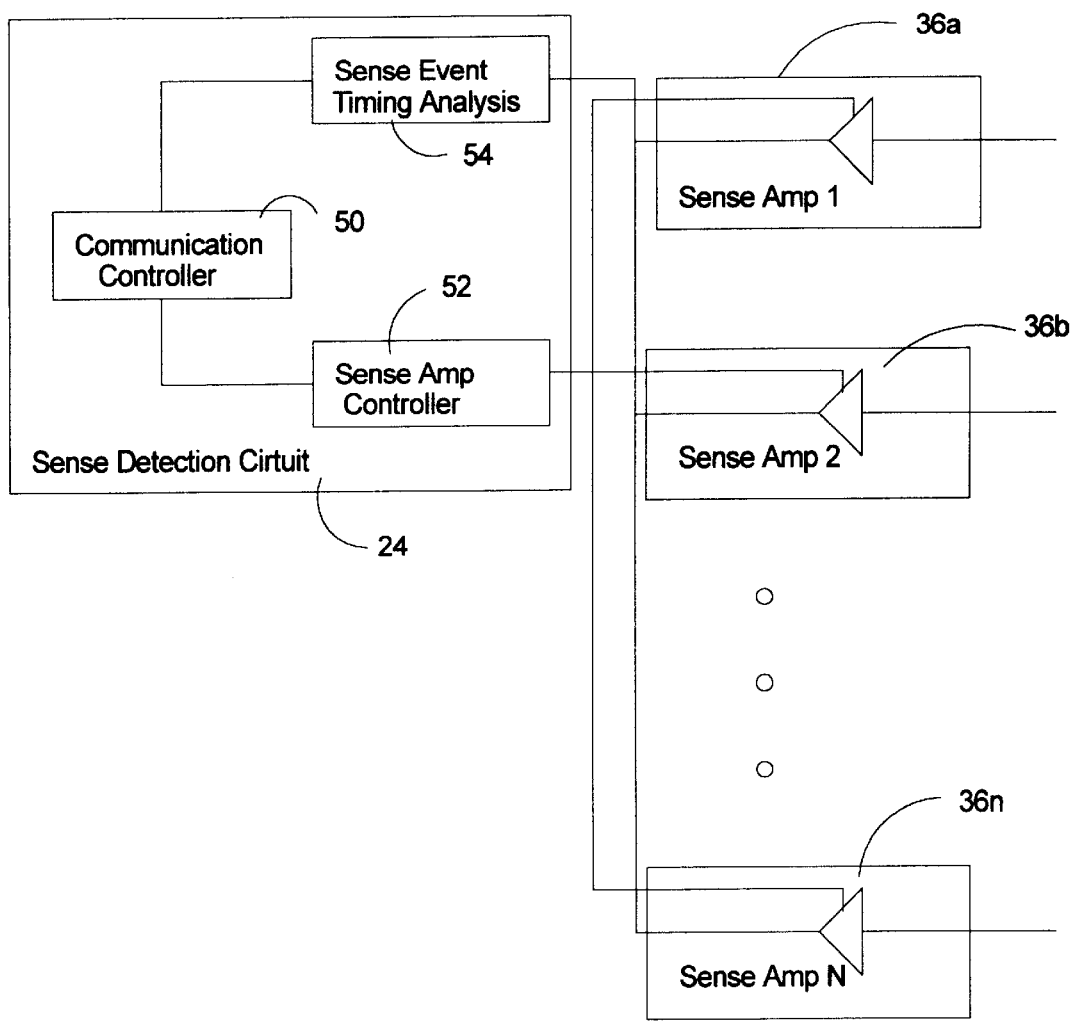
FIG. 5 is a block diagram of another portion of the circuits of FIG. 2.

A variety of apparatus may also be used to sense signals from multiple electrodes through the sense detection circuit 24. A first embodiment is illustrated in FIG. 5. In the embodiment of FIG. 5, a communication controller 50 in the sense detection circuit 24 communicates with the logic control and timing circuit 22 (FIG. 2). The communication controller 50 is in electrical communication with a sense amp controller 52 and a sense event timing analysis unit 54. The sense amp controller 52 regulates amplification levels on the sense amps 36a, 36b . . . 36n such that significant signals are detected and noise is rejected. Each amplifier has independent sensitivity (gain) and filter characteristics. The sense event timing analysis unit 54 receives output from the sense amps 36a, 36b . . . 36n and collects that information into a description of a moving wave front. Both intervals between sensed events and the sequence of channels or electrodes are used to describe the wave front. The description of the wave front is communicated to the logic control and timing circuit 22 for use in determining the appropriate therapy. A second embodiment, illustrated in FIG. 6, employs a multiplexer in a manner similar to the second embodiment of the output control circuit, described in connection with FIG. 4, above. In this second embodiment of the sense detection circuit 24, the sense amp controller 52 controls a single amplifier 56. The sense event timing analysis unit 54 analyses the output of the single amplifier 56 and produces the description of the moving wave front. A sense timing controller 58, in electrical communication with both the communication controller 50 and the sense event timing analysis unit 54, controls a multiplexer 60 through a switch matrix controller 62. The switch matrix controller 62 opens and closes a plurality of switches 64a, 64b . . . 64n, selectively connecting the electrodes of the lead 14 to the sense amplifier 56. As explained above, replacing multiple dedicated sense amplifiers 36a, 36b . . . 36n with a single amplifier 56 exchanges flexibility and simplified control for energy efficiency.

Figure 6:
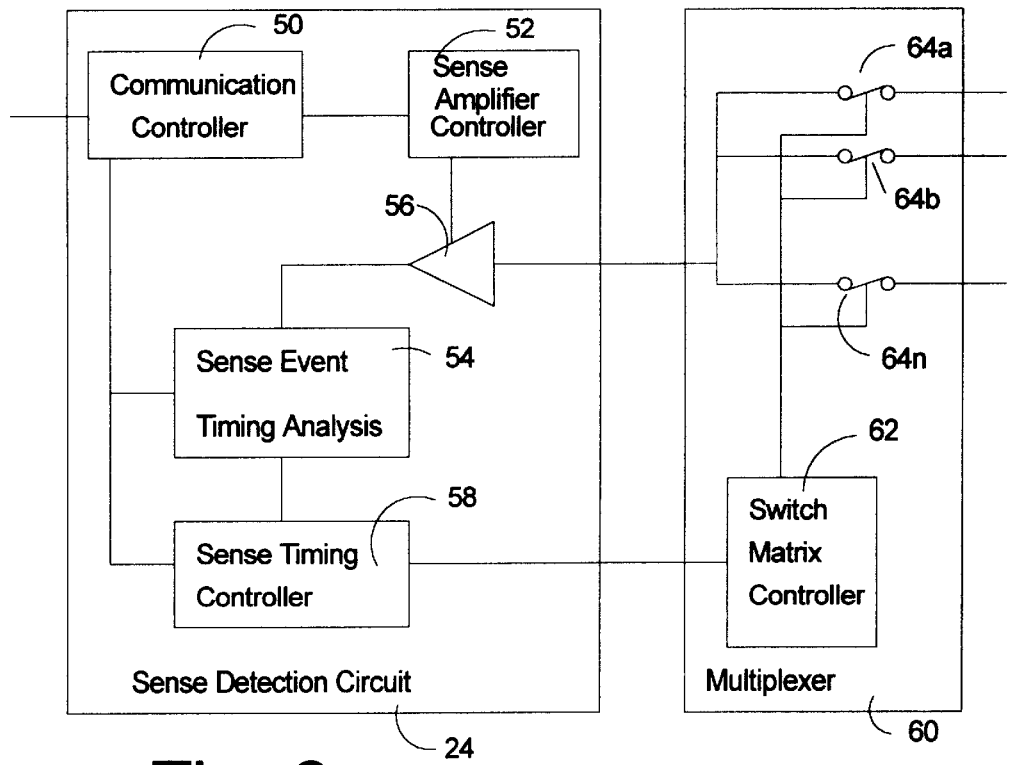
FIG. 6 is a second embodiment of the other circuit portion of FIG. 5.
Figure 7:
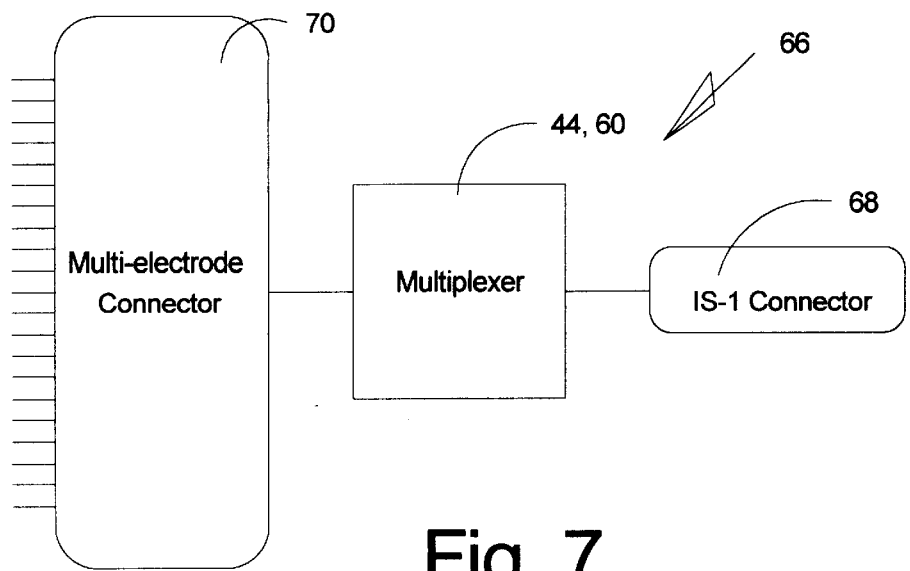
FIG. 7 is a block diagram of an adapter for connecting a multi-electrode lead to an IS-1 connector.

The multiplexers 44, 60 of the embodiments of the output control circuit of FIG. 4 and of the sense detection circuit of FIG. 6 may be combined externally to the cardiac stimulator 12 in an alternative configuration, illustrated in part in FIG. 7. FIG. 7 shows an adapter 66 for a connecting a multi-electrode lead to a cardiac stimulator having an IS-1 connector in the header of the stimulator 12. IS-1 connectors are well known and many physicians are familiar with their operation and use. For the adapter 68 a male IS-1 connector 68 is connected to the multiplexers 44, 60 in an independent package. The multiplexers are connected either directly to the lead 14 or indirectly through a multi-electrode connector 70. Dual chamber pacemakers having two IS-1 connectors in a single header are well known. In cardiac stimulators 12 according to the present invention using IS-1 connectors rather than a specialized multi-electrode connector, a first IS-1 connector might be used to carry both the voltage from the voltage amp 42 and signals from the pulse timing circuit 38 and a second IS-1 connector might be used to carry both the signals to the sense amplifier 56 and the control signals from the sense timing controller 58. Alternatively, one IS-1 connector might be dedicated to the control signals from the sense timing controller 58 and the pulse timing circuit 38 while another IS-1 connector might be dedicated to the signals delivered to and received from the heart, that is, to pulses from the voltage amp 42 and to sensed events.

Multi-Electrode Lead

Details of the multi-electrode lead 14 are shown in FIG. 8. In a second embodiment, the lead 14 includes an external biocompatible polymer tube 72 having a straight portion 74 and a shaped portion 76. The tube may be made of polyurethane or other similar materials that may be thermally shaped so that the shaped portion 76 retains any desired configuration. In FIGS. 1 and 8, the shaped portion 76 is shown as having a spiral shape, but many other shapes may be selected as well. The spiral or coil shaped lead of FIGS. 1 and 8 places electrodes around the entire chamber of the heart. This embodiment allows complete sensing and stimulating control around the entire chamber.

Another embodiment illustrated in FIG. 9 may provide a folded lead that places electrodes along the ventricular septum and up into the right ventricular outflow tract. This embodiment may be particularly useful where the applied therapy seeks to stiffen the septum, as further described below.

Figure 10:
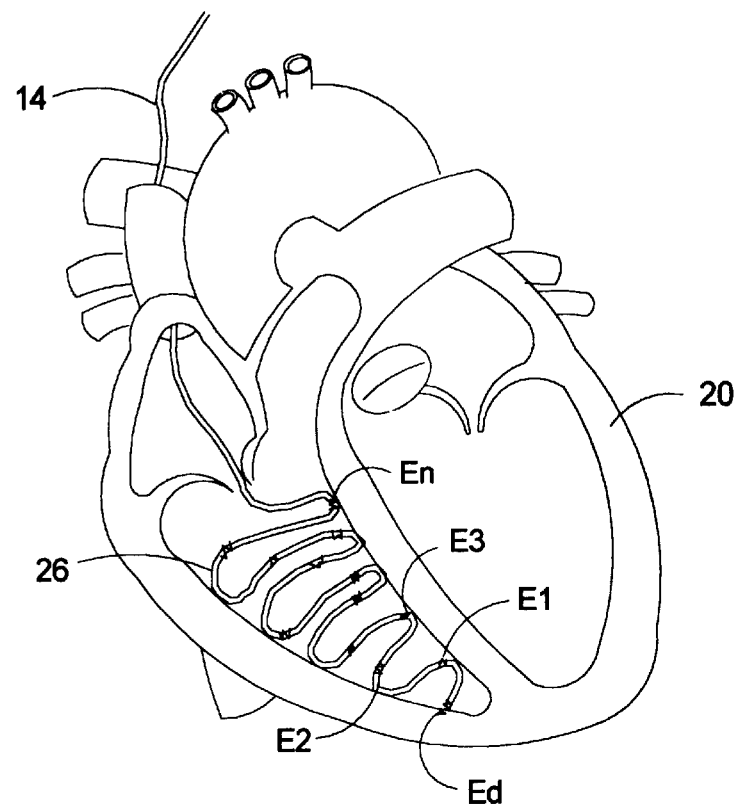
FIG. 10 is a view of a third configuration of the multi-electrode lead in the heart.
Figure 11:
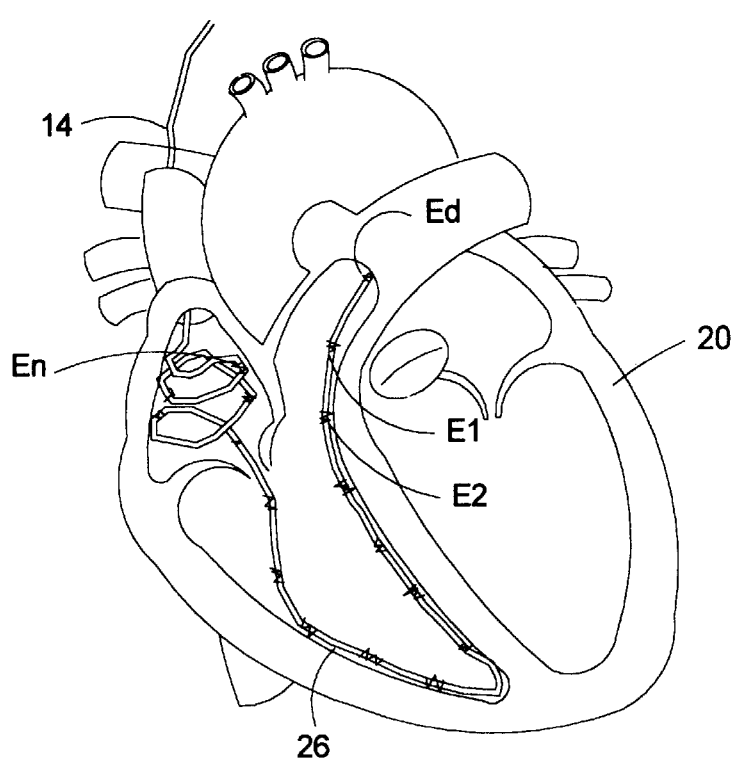
FIG. 11 is a view of a fourth configuration of the multi-electrode lead in the heart.

Yet another possible embodiment of FIG. 10 uses a serpentine shape to place electrodes along a wall of a chamber of the heart. These and other configurations may be combined and used in one or more chambers of the heart. FIG. 11, for example, shows a lead having a folded configuration in the right ventricle and a coiled or spiral configuration in the atrium. Such a configuration may have particular advantages for so-called single pass, dual chamber applications.

It will be apparent that numerous shapes could be selected to address the clinical needs of a particular patient. Moreover, because the position of the electrodes in the heart is determined as much by physiology and implantation technique as by the characteristics of the lead, the effectiveness of the electrodes is best determined after implantation and is substantially independent from the location of a given electrode along the lead. Apparatus and methods for identifying optimum electrodes are therefore described hereinafter.

Attached to tube 72 of the lead 14 of any configuration, there are provided a plurality of electrodes E1, E2, E3, E4, E5 . . . En. Preferably electrodes E1 . . . En are formed of coils of bare wire or cable wound about the tube 72. Each electrode is connected to corresponding wires W1, W2, W3 . . . Wn which extend through the length of tube 72 and which are shown exiting through end 80 for the sake of clarity. Wires W1, W2, W3 . . . Wn are insulated, so that they are not shorted to each other within the tube 72. The electrode 14 and its method of manufacture are disclosed in co-pending commonly assigned application Ser. No. 09/245, 246 filed Feb. 5, 1999, and incorporated herein by reference. Preferably the end 80 of tube 72 and the ends of wires W1, W2, W3, etc. are coupled to a connector 82 for attaching the lead 14 to the cardiac stimulator 12. The connector 82 may have a plurality of pins Pi. Each wire W1 . . . Wn is associated with a pin. As explained below, however, it is not necessary to connect the electrodes E1 . . . En through the wires W1 . . . Wn to any specific pin. Because the lead may assume different configurations in the heart, it is the relative location of the electrodes in the heart that is important for application of an appropriate therapy, not the placement of the electrodes along the lead. This apparatus, therefore, assigns a functionality to an electrode and its pin after implantation of the lead.

In addition to spiral coil or ring electrodes E1 . . . En, a distal tip electrode Ed may also be provided. The distal tip electrode Ed may also have an active fixation mechanism, for example a helical screw 84 or tines, to secure the lead to the interior wall of the heart.

The lead 14 can be constructed with the tube 72 extending relatively straight or can be customized to any shape to fit any pre-selected location within the heart 20 dependent on each particular patient's pathology. For example, if the lead 14 is to be placed in the greater cardiac vein, then its end 16 (consisting of tube portion 76 and electrodes E1, E2, E3 . . . etc.) is shaped to form a small helix, so that it will fit into the grater cardiac vein.

The tube 72 can be formed with a longitudinal cavity 86, as shown in the cross sectional view of FIG. 12. Cavity 86 holds the wires W1, W2, W3 etc. The lead 14 could be straightened by inserting a substantially straight stylet 90 into cavity 86. The stylet 90 is also flexible but is less flexible than the lead 14 so that as it is inserted into the cavity 86, it forces the tube 72 to straighten. The lead 14 is then inserted into the heart or into a vein near the heart. After implantation of the lead 14, the stylet 90 is withdrawn and the lead 14 flexes back and takes a configuration shown, for example, in FIG. 8, 9, 10, or 11.

Programmer

A programmer 100 may be used to program the cardiac stimulator 12, usually by electromagnetic signals. In particular for use with this system, the programmer may be temporarily connected directly to the lead 14, as shown in FIG. 1 by dotted line 102. This connection may be made to the lead alone, or it may be made through the cardiac stimulator 12. This connection is used after the lead has been implanted to characterize the location of the electrodes, as explained in detail below. The programmer 100 comprises a microprocessor 104 for performing various functions in connection with programming the cardiac stimulator. In addition, in order to characterize the electrodes of the lead, and provide sufficient information for selecting therapies suitable for treating congestive heart failure, the programmer may be provided with certain sensors and pulse or frequency generators. The programmer may have an external ECG detector coupled to electrodes 110, 112, which may be external electrodes. In addition, a physiologic sensing circuit 114 may be provided with an associated sensor 116. Physiologic parameters associated with cardiac performance may be sensed to provide information for characterizing the lead or programming the cardiac stimulator. Such physiologic parameters may include blood pressure, temperature, blood oxygenation, and so on. Similar sensors may be connected to the cardiac stimulator 12 for chronic implantation and may be mounted on the stimulator itself or on the lead 14, for example. The programmer may also be provided with a pulse generator for generating temporary stimulating pulses, if desired or if pulses are not generated by control of the cardiac stimulator and the cardiac stimulator is not connected to the lead during characterization of the lead. In this context, the programmer may also have sensing circuits 120 for sensing electrical events in the heart where the cardiac stimulator 12 is not used for this purpose. Finally, the programmer may have a high frequency generator 122 and high frequency sensor circuit 124, for providing non-stimulating high frequency signals that may be used to calculate the three dimensional positions of the electrodes within the patient's heart.

A cardiac visualization device 101 may also be provided. The device 101 may be a fluoroscope or ultrasonogram apparatus. The device may be capable of visualizing Doppler flow of blood through the valves of the heart and in particular through the mitral valve. As will be explained hereafter, motion of the septal wall may be visualized for treatment of congestive heart failure and in particular for the selection of an optimal set of stimulating electrodes. A sensor 103 emits and detects radiation such as ultrasound or electromagnetic radiation. The resulting images may be digitized and communicated to the microprocessor 104 by a communications link 105. Alternatively, an operator may select optimal electrodes through the microprocessor based in part on data displayed by the visualization device.

Electrode Identification

The process of identifying the optimum electrode or electrodes or a pattern of electrodes may be performed using several different approaches. For treatment of congestive heart failure, as well as for more traditional pacing modalities for bradycardia and tachycardia, the location of the electrode in the heart is important, not necessarily the position of any given electrode along the lead. As is apparent from FIGS. 8, 9, 10 and 11, an implanted lead may assume many configurations. The lead may overlap itself, whereby electrodes proximal on the lead are closer to the venticular apex than are more distal electrodes. However, in many cases, the relative location of the electrodes in the heart may be determined by inspection under fluoroscopy by visual approximation. This information or mapping would be used either in the programmer or the cardiac stimulator or both. The mapping could be used as a starting point for additional location algorithms or as a model for measuring cardiac performance or providing appropriate therapy.

The connection between electrodes and pins may be determined either by manufacturing such that the first electrode is connected to the first pin, the second electrode to the second pin, and so on, or by measurements. A test apparatus may be provided wherein an electrical signal is supplied to each electrode in turn and the pins sampled to identify the pin receiving the signal. The mapping of electrodes to pins would then be communicated to a cardiac stimulator at the time of implantation so that the lead and cardiac stimulator could function together as a unit.

The relative position of the electrodes can also be determined by measuring certain phenomenon and calculating a three dimensional position for each electrode, or by sensing the progression of an intrinsic wave front propagating through the heart, or by sensing the progression of a stimulated wave front, moving through the heart, as described below.

Figure 13:
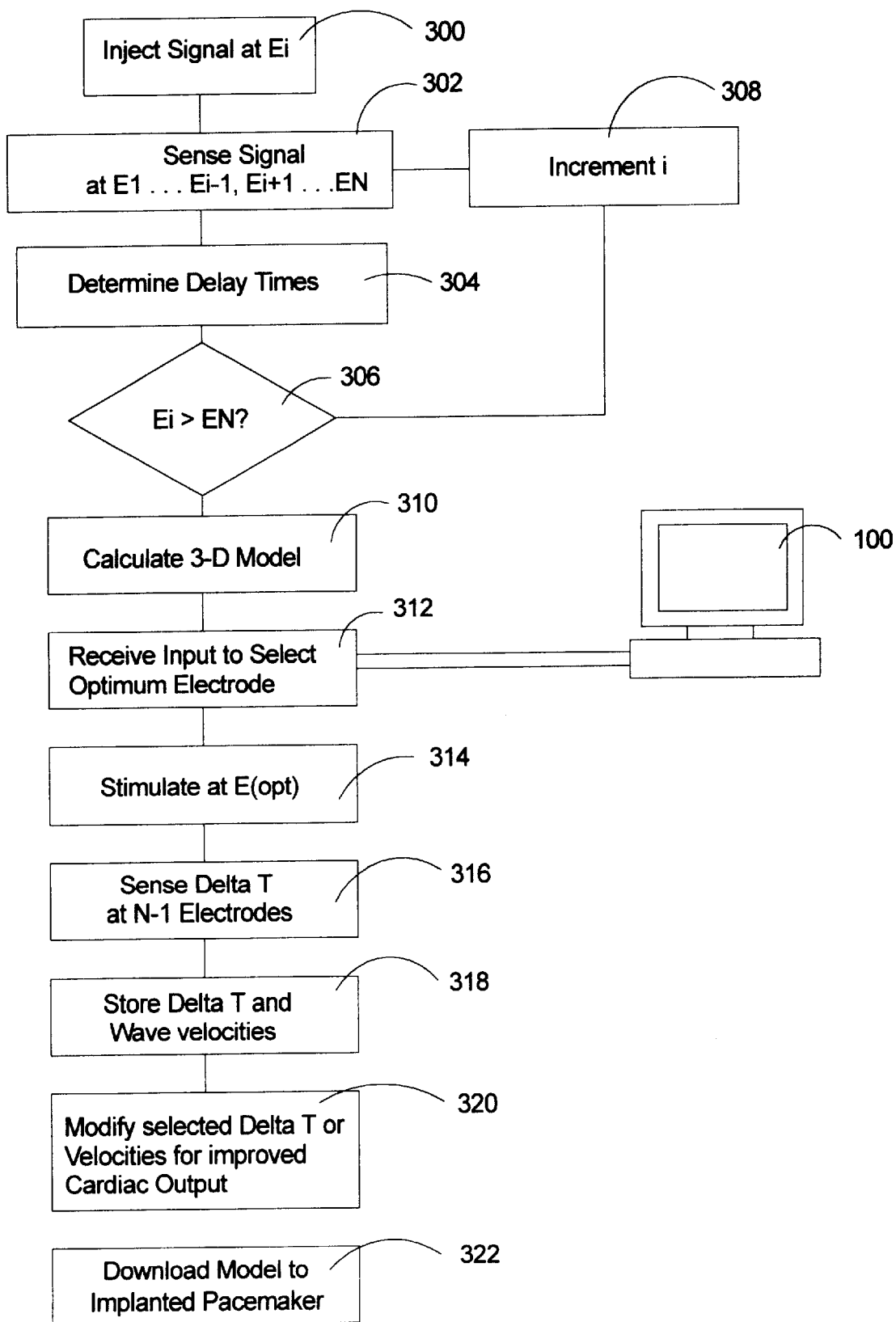
FIG. 13 is a flow chart for the development of a 3-D model of electrode position.

To determine the relative positions of the electrodes in three-dimensional space, calculations can be performed either in an external device such as the programmer 100, or in the cardiac stimulator 12. Because such calculations may be relatively energy expensive, calculation in an external device may be preferred. As described above, after implantation, the free end of lead 14 is connected to programmer 100, as shown in dotted line 102 in FIG. 1. Next, in step 300 (See FIG. 13) a high frequency test signal is fed to one of the electrodes, Ei, such as the electrode disposed at the tip of the lead 14. Preferably this test signal has a frequency in a range that is known to have no effect on the heart 20. For example, the test signal may have a frequency of about 200 kHz. This test signal is generated by a high frequency or HF generator 124 and applied to the lead 14 by a multiplexer 126 that selects different electrodes. While this HF test signal is applied to the one lead electrode, a sensor 124 within the programmer 100 is used to detect 302 the HF signals in the remaining electrodes. In step 304, a microprocessor 104 is used to determine the voltage amplitude of the detected signals at each electrode. If a signal has not been injected at each of the n electrodes (step 306), a new electrode i is selected (step 308), and a new set of data is recorded. Selecting all n electrodes will produce a more accurate determination of the position of the electrodes, however, positions can be determined by selecting as few a five electrodes (step 308). Using this information, the microprocessor 104 then determines (step 310) the position of each electrode in step 300. Details of the algorithms used to make this determination are provided in commonly assigned co-pending application Ser. No. 60/288,358 filed May 3, 2001 and entitled "Implantable Electrode System To Map Electrical Activity In 3-Dimensions And Deliver Multifocal Pacing Therapy For Atrial Fibrillation", incorporated herein by reference. Briefly, as described in that application, a 3D electrode positioning system operates by applying a periodic voltage to several subgroups of the electrodes and measuring the signal induced on selected remaining electrodes. The number of subgroups employed is sufficient to over-determine a system of non-linear equations representing the distribution of the voltage (or potential) at each of the electrodes and in the surrounding tissue. Several means are available to extract the electrode positions relative to tissue boundaries from such models. One of these, the method of non-linear least squares, is well known in the literature. (e.g. Golub and Van Loan, Matrix Computations, 1989, Johns Hopkins)

In step 312, families of sensing and pacing electrodes are designated. This may be done automatically, using predetermined rules provided in programmer 100. Alternatively, a physician using an input device 106 may designate electrodes based on the position of the electrodes and other criteria. Using this process, it may be determined for example, that the electrodes E1–E6 of FIG. 8 should be used for ventricular pacing.

After the optimum stimulating electrode has been designated, the cardiac stimulator or the programmer 100 may stimulate 314 the heart and sense 316 the propagating wave front at each of the remaining N-1 electrodes. The time delay from the origin of the inserted signal until the signal is sensed at an electrode provides a set of delta times representative of the preferred propagation of a wave front across the heart. The time delays and position for an electrode permits calculation of a wave velocity 318 across the heart. A physiologic sensor, such as a sensor for cardiac contraction, or for core temperature, or blood oxygenation can be used to determine if the selected electrode is physiologically optimum. Alternatively, an external cardiac sensor, such as heart monitor 108, may be used to detect the external electrocardiogram resulting from the stimulation at the optimum electrode. Comparing the detected ECG with an ideal ECG, an attending physician may attempt to modify 320 the stimulation pattern. This may be done in conjunction with the programmer 100. The physician, for example, may indicate through a graphical interface, a portion of the ECG that should be modified. The programmer may then seek to stimulate the heart at selected other electrodes after the primary stimulation. Thus, by shortening the allowed Delta Time between the origin electrode and another electrode, an advancing wave front could be accelerated or otherwise modified. Improved cardiac performance may be detected on the physiologic sensors or through the detected external ECG. When a satisfactory stimulation pattern has been identified, the parameters representing the stimulation pattern may be communicated 322 to the implantable cardiac stimulator. Parameters may include time delays (Delta T), wave front velocities, three-dimensional coordinates, and pin assignments. Pin assignments tell the implanted device which pin in the lead connector is associated with an electrode at a particular location in the heart. As noted above, the location of the electrode along the lead is not important.

Information on the relative three dimensional location of electrodes in the heart and with relationship to the heart wall may be valuable in specifying a therapy for the diseased heart or for interpreting phenomenon detected in the heart. Such information is not absolutely necessary for providing therapy for congestive heart failure. A set of ordered time delays as a function of the n electrodes implanted in the heart may be sufficient to provide a clinical benefit. The order of the electrodes and their associated time delays may be determined in several ways. Two such ways are illustrated in FIGS. 14 and 15.

Figure 14:
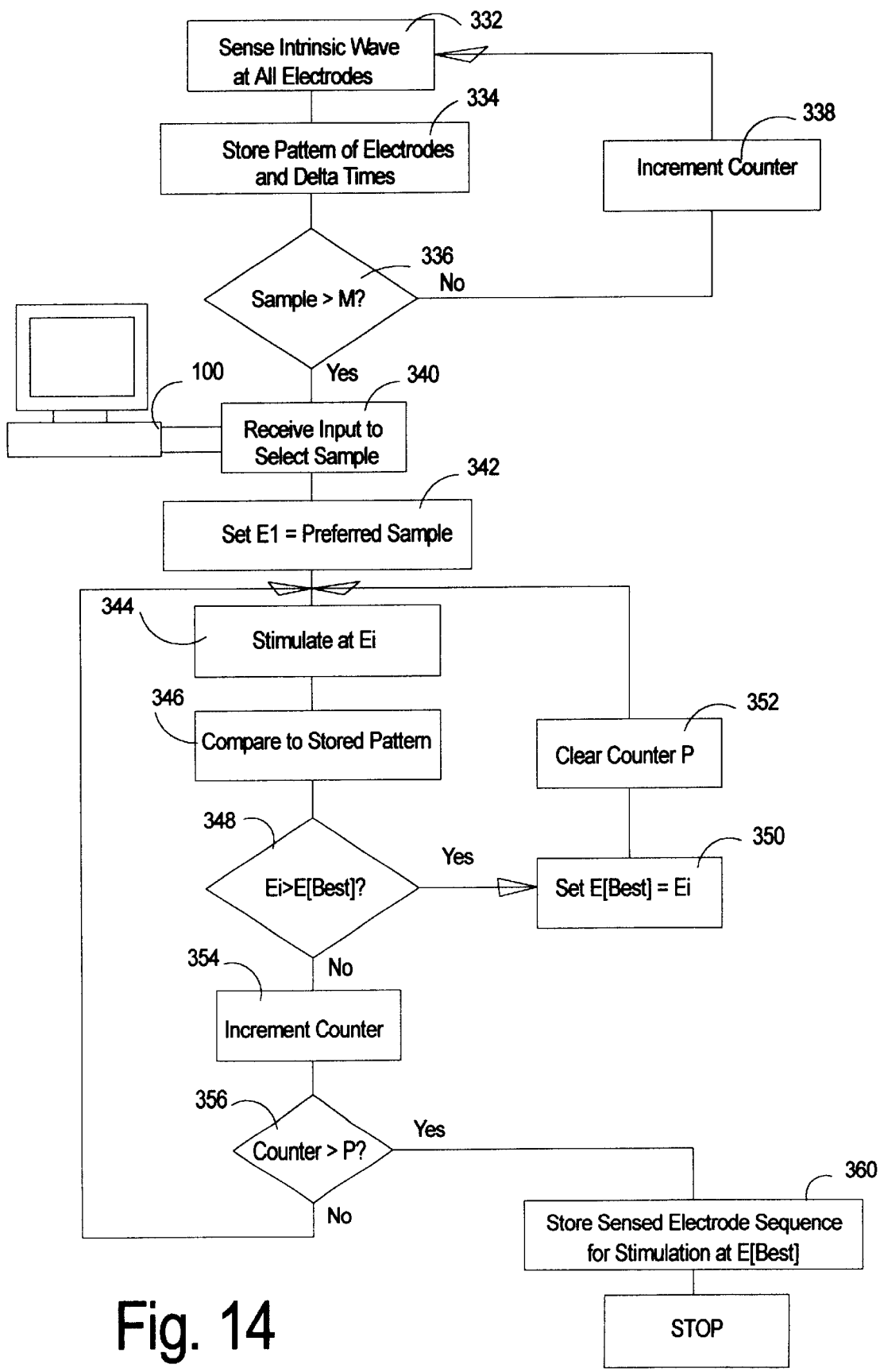
FIG. 14 is a flow chart for characterizing electrodes from intrinsic wave fronts.
Figure 15:
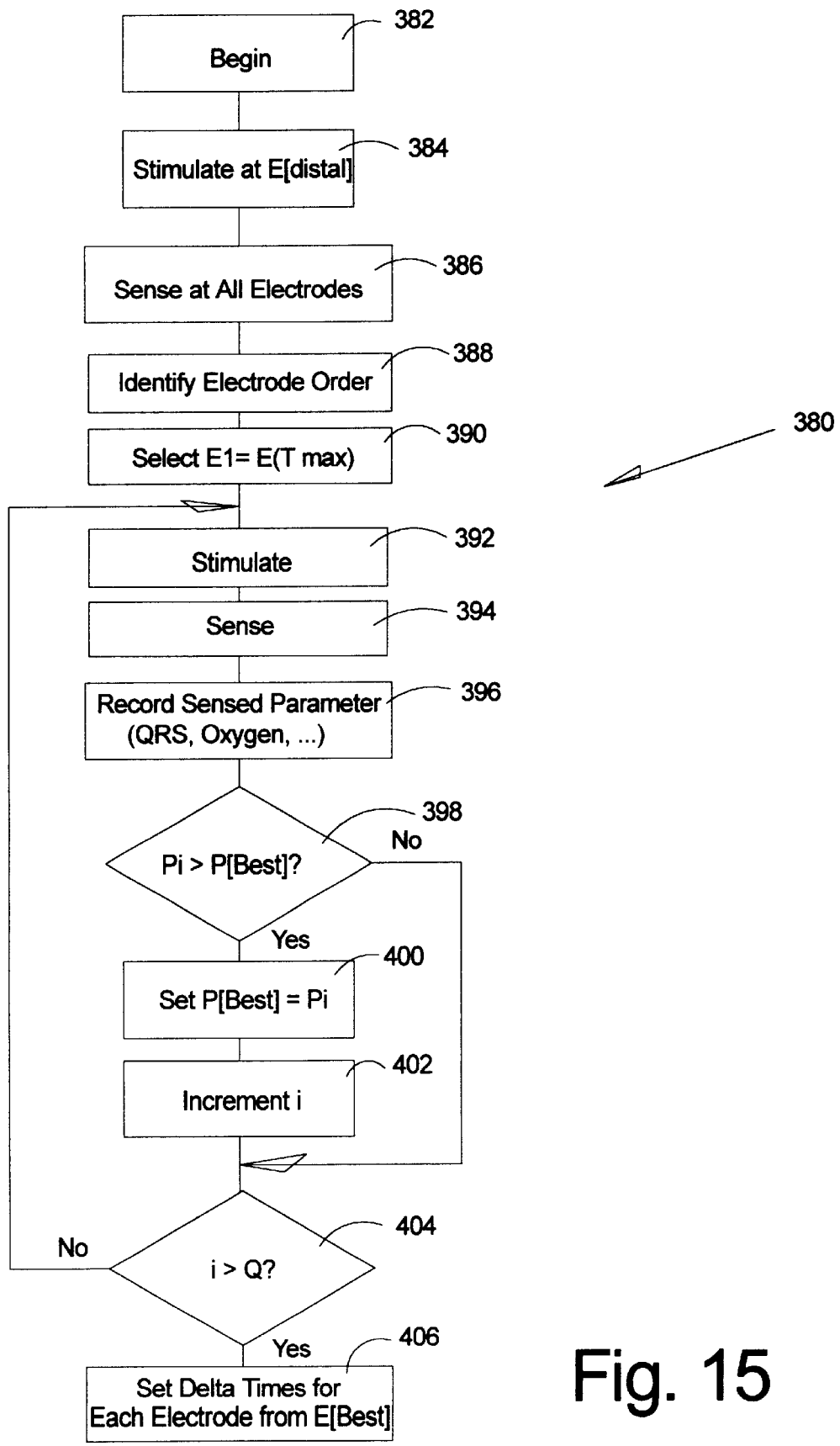
FIG. 15 is a flow chart for characterizing electrodes from wave fronts produced by stimulation.

In FIG. 14, a system 330 is illustrated, for patients with at least some intrinsic cardiac function, that is, wherein a relatively normal contraction wave front is expected to propagate across the heart. As above, although this functional system could be implemented on the implanted device, for reasons of energy conservation, implementation on the programmer 100 is preferred. To initialize the system, the patient's intrinsic cardiac contraction is sensed 332 at all n electrodes implanted in the heart. Ordered pairs of an electrode and a time delay Delta T are stored 334 for each of the n electrodes. As pointed out above, this may involve the identification of a pin number in the lead connector. Because the pins are not necessarily sequentially associated with adjacent electrodes on the lead, and further because the position of the lead in the heart is somewhat random, no information can be drawn from the physical order of the pins in the connector as distinct from the logical order of the pins (and electrodes) determined from sensing the wave form in the heart. In may be expected that the wave front pattern in a diseased heart varies considerably. Therefore, a sample 336 of a pre-selected number M of contractions may be taken. A counter 338 may be incremented until the sample has been filed. Thereafter, the most physiological appropriate occurrence may be selected 340. This may involve comparing the samples to an ideal template, statistically averaging the samples, or presenting the stored data to a physician through a communication device or programmer 100, and allowing the physician to select an intrinsic waveform among the M recorded waves. The physician may be assisted in the selection by additional sensor information associated with the wave forms, for example, the external ECG, blood oxygenation, blood pressure, and so on.

When the preferred sample is identified, the associated set of ordered pairs of electrodes and time delays is set 342 as an initial preferred condition. This set of electrodes will usually approximate a desirable wave front preceding from the sinoatrial node down through the heart to the apex of the ventricle. In particular, the first electrode E1 in this series located in a given chamber of the heart, for example, in the right ventricle, is taken as the first approximation of the optimum electrode for stimulation in that chamber. Under appropriate circumstances, the heart is stimulated at E1 (step 344). The resulting contraction is sensed at the remaining n-1 electrodes, and the resulting vector (that is, set of ordered pairs of electrodes and time delays) is compared 346 to the stored pattern. A search is performed to confirm that stimulation at E1 is superior to any electrodes within a predetermined proximity to E1. Since the actual physical location of the electrodes is unknown, this is a logical proximity, that is, for example, the first P electrodes in order of time delay from E1. If stimulation at one (Ei) of these P electrodes is superior to E1 (step 348), Ei replaces E1 as the preferred electrode E[Best] (step 350). The counter is reset 352 and the search proceeds in the proximity of the new preferred electrode. Otherwise, the counter is incremented 354. When the counter reaches the pre-selected number P (step 356) the search halts and E[Best] has been identified 360.

It may also be necessary to identify the optimum electrode E[Best] when there is no intrinsic waveform or when the intrinsic waveform is so unpredictable or sporadic that meaningful information cannot be derived from it. In such conditions, a system 380 illustrated in FIG. 15 may be used. As mentioned above, a multi-electrode lead used with this apparatus may be constructed such that the electrical communication between an electrode and a pin in the lead connector is essentially randomly determined at the time of manufacture. That is, the electrodes may be connected to the pins in any order. However, if the distal tip of the lead is both a fixation device, such as a helical screw, and an electrode, the distal tip will preferably be provided with an identifiable electrical connection, probably physically different from the other wires in the lead. For example, the other electrodes may be mechanically continuous with their electrical connector or wire, while the distal tip or distal electrode may be connected to a conducting wire through a mechanical connection, such as a crimp joint or laser weld. This difference would allow the distal electrode to be electrically connected to a specific pin in the lead connector. Inserting the electrical conductor for the distal electrode into the lead either first or last could also aide in identifying this connection. In addition, the conductor connected to the distal tip could be physically different from other conductors, for example in type, color or thickness of wire or insulation. The conductor connected to the distal tip might also be identified electrically.

When the lead is implanted, the distal tip or distal electrode can usually be located physically in the heart. For instance, the distal electrode may be implanted low in the heart at the apex of the right ventricle. The system 380 can begin 382 to identify an optimum stimulation pattern. A signal may be emitted 384 through the distal electrode E[Distal]. The signal may be either a high frequency, non-stimulating signal, or a stimulating pulse that causes the ventricle to contract. The propagation of this signal through the heart is sensed 386 at all electrodes and elapsed times Delta T for each electrode are recorded 388. It may be expected that the electrode associated with the largest Delta T would be located relatively high in the ventricle. It may not be the optimum electrode, but it represents a good candidate for beginning a search for the optimum electrode. Therefore, Ei is set 390 equal to E[max T], and the heart is stimulated at step 392. The resulting waveform is sensed 394 either by the implantable device or externally. A physiologic performance parameter is also sensed 396 during the cardiac contractions affected by the stimulation. The sensed parameter Pi is compared 398 with a standard P[Best]. If Pi exceeds P[Best], P[Best] is replaced by Pi in step 400. The next potential electrode is identified by incrementing i [step 402]. A new set of ordered pairs associating each electrode (or pin) to a Delta T resulting from the stimulation. If i has been incremented to Q (step 404) the set of ordered pairs or Delta T values is stored 406. Q is a pre-selected number equal to of less than the total number of electrodes. If i is less than Q, a new stimulation 392 is produced at the next Ei electrode. When the optimum electrode E[Best] has been electrode, a physician may choose to modify the shape of the waveform by adding additional stimulations at other electrodes, in the manner described above.

The selection of optimal electrodes has been described in conjunction with pacing of the right ventricle. However, the same techniques may be used for other types of stimulations as well, including atrial pacing, dual chamber pacing, atrial and ventricular cardioversion, atrial defibrillation, etc. Moreover, while the techniques are described in conjunction with a single multi-electrode lead, they are applicable for leads having other configurations, such as several single or multi-electrode leads.

Therapies for Congestive Heart Failure

When the cardiac stimulator is in operation, the sense detection circuit 24 and sense amplifiers 28 collect information about wave fronts moving through the heart. This information can be compared to optimized patterns or templates, such as those developed above, and used to provide therapy. The information can also be stored for diagnostic purposes.

For example, the cardiac stimulator 12 can distinguish between intrinsic contractions and ectopic contractions by distinguishing events that originate near the normal focus, that is, near the SA node in the atrium or near the AV node in the ventricle. Where an optimum or best electrode has been identified as near one of these foci, as described above, a sense event may be first detected by the optimum electrode or by an electrode within a predetermined proximity of the optimum electrode. Such a sensed event would be considered intrinsic if sensed first at the optimum or best electrode or by one of a pre-selected set of nearby electrodes. Events initiating from locations remote from the foci, that is, relatively far away from the optimum electrode or its adjacent set of electrodes, would be considered ectopic. A list of frequency of initiation at each electrode can be maintained in memory in the cardiac stimulator as a useful diagnostic.

Using the multi-electrode lead and capabilities of the apparatus described above, it is possible to map cardiac electrical activity. For example, in FIG. 16, a series of sense events is illustrated at electrodes numbered in order of physical location within the heart from electrode 1, which is the electrode nearest the relevant focus for a particular chamber of the heart. The wave front proceeds across the heart in an orderly fashion, corresponding to the surface ECG also shown in FIG. 16. The progress and shape of the wave front may be represented by a series of ordered pairs, each pair comprising a number of an electrode and a time delay in milliseconds, representing elapsed time from the prior sensing point or electrode. As an example, the wave front series or matrix for the samples of FIG. 16 might be:

| Electrode | 1 | 2 | 3 | 4 | 5 | ... | N |
|---|---|---|---|---|---|---|---|
| Time (ms) | 0 | 20 | 20 | 10 | 15 | | t |

Figure 17:
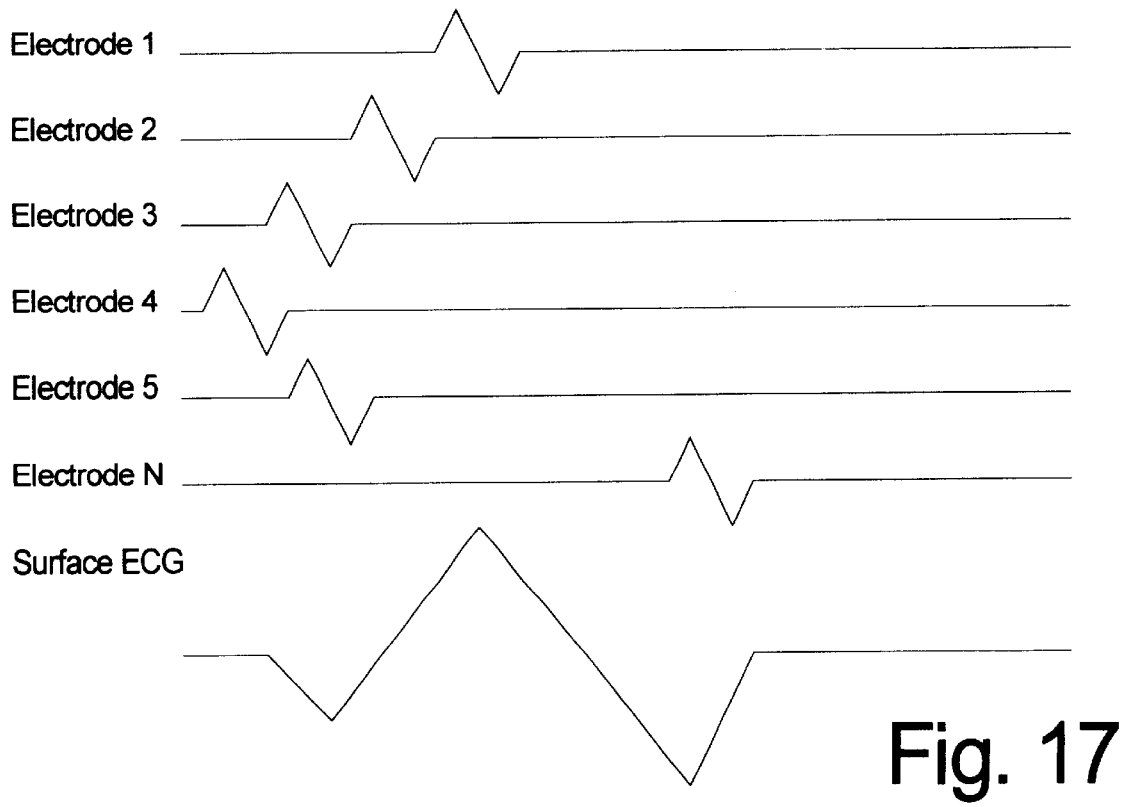
FIG. 17 is a graphical representation of an ectopic cardiac contraction as sensed by a plurality of electrodes and by an external ECG machine.

In contrast, an ectopic event might produce a pattern, similar to the pattern illustrated in FIG. 17. The contraction commences near electrode 4, and propagates towards both electrode 3 and electrode 5. The matrix may appear as follows:

| Electrode | 4 | 5 | 3 | 2 | 1 | ... | N |
|---|---|---|---|---|---|---|---|
| Time (ms) | 0 | 40 | 5 | 30 | 45 | | t |

In ectopic contractions, the surface ECG may be longer or less well-defined, reflecting the decreased efficiency of such contractions. As will be explained below, the cardiac stimulator 12 can count intrinsic and ectopic contractions and, by recording the ordered pairs or matrix for a contraction, can record the pattern of ectopic events for diagnostic purposes.

Figure 16:
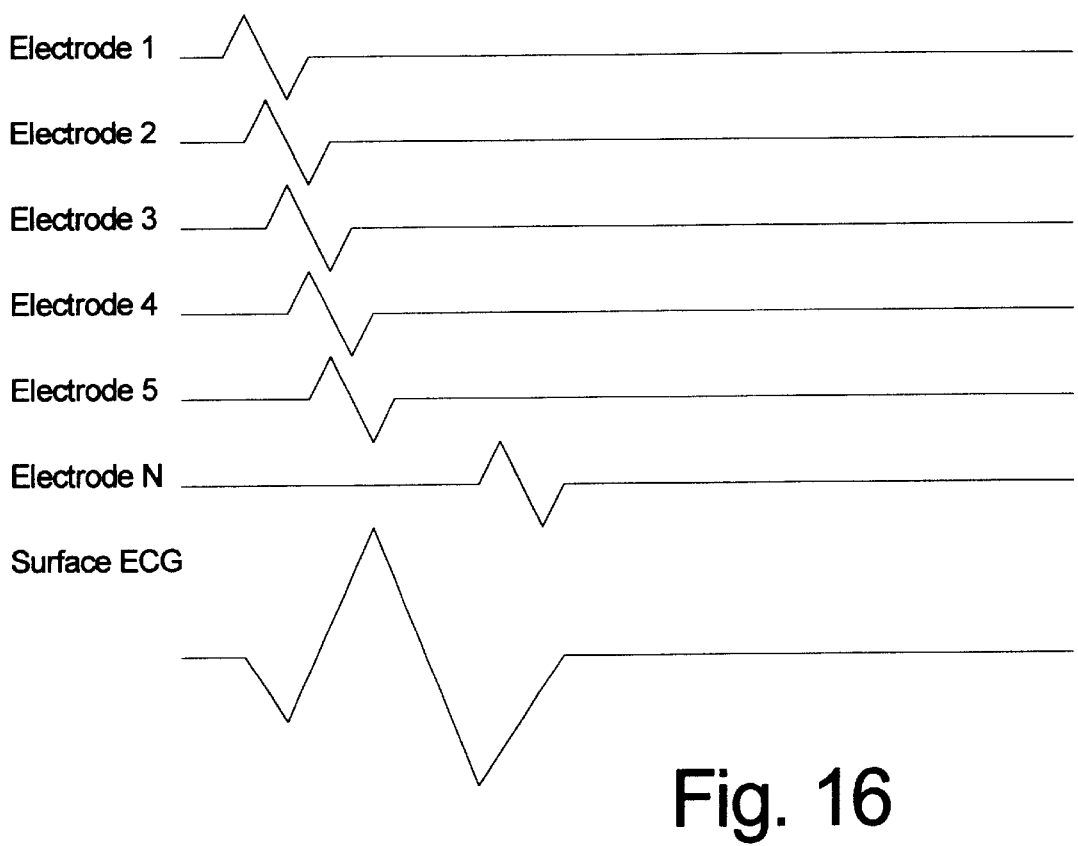
FIG. 16 is a graphical representation of a cardiac contraction as sensed by a plurality of electrodes and by an external ECG machine.

The pattern of FIG. 16 represents the wave front of a normally conducted ventricular contraction. In patients suffering congestive heart failure, the wave front and contraction may differ from the normal pattern. The wave front may commence at an ectopic site. The wave front may be delayed or may be ineffectual in certain locations, or it may not propagate uniformly through the heart. In any event, the heart chamber does not contract efficiently, and the heart has to work harder, for less effect. Controlled pacing through multiple electrodes can treat these conditions. The cardiac stimulator and multiple electrode lead described herein can deliver effective therapy for alleviating congestive heart failure.

Figure 18:
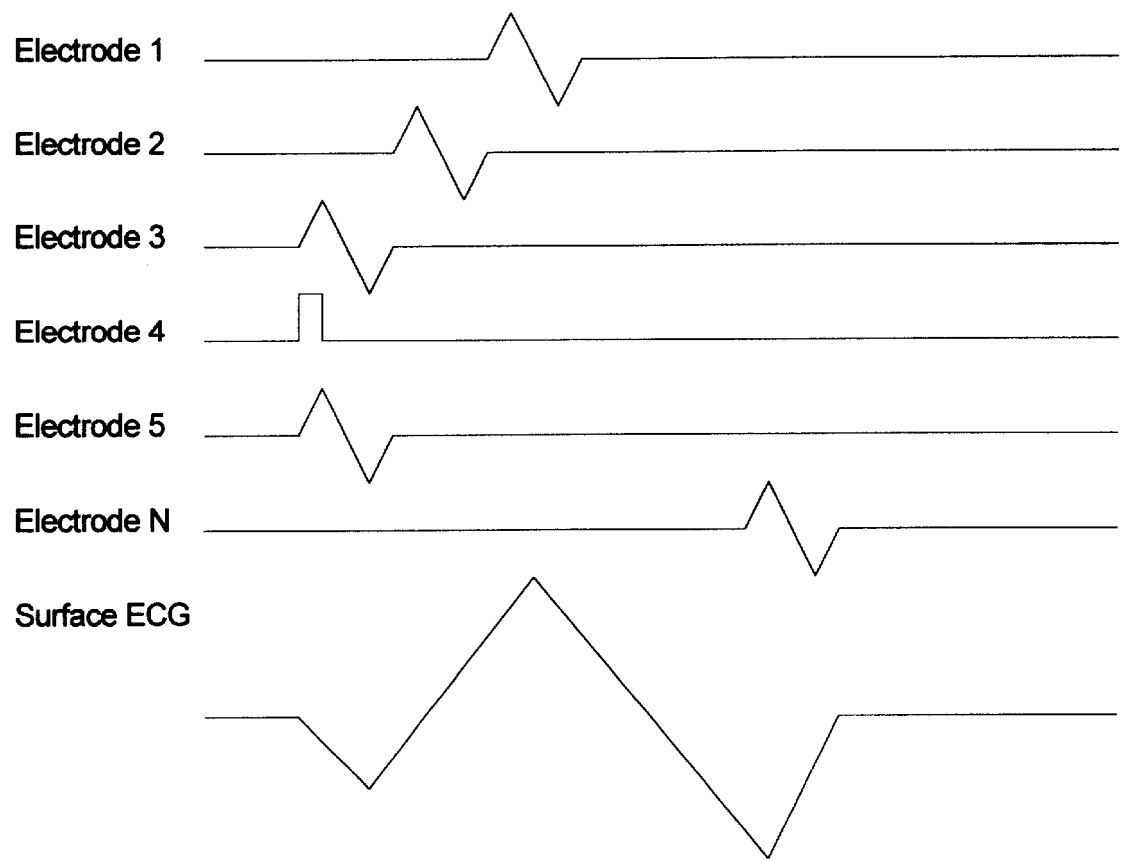
FIG. 18 is a graphical representation of a cardiac contraction caused by pacing at a sub-optimal electrode as sensed by a plurality of electrodes and by an external ECG machine.
Figure 19:
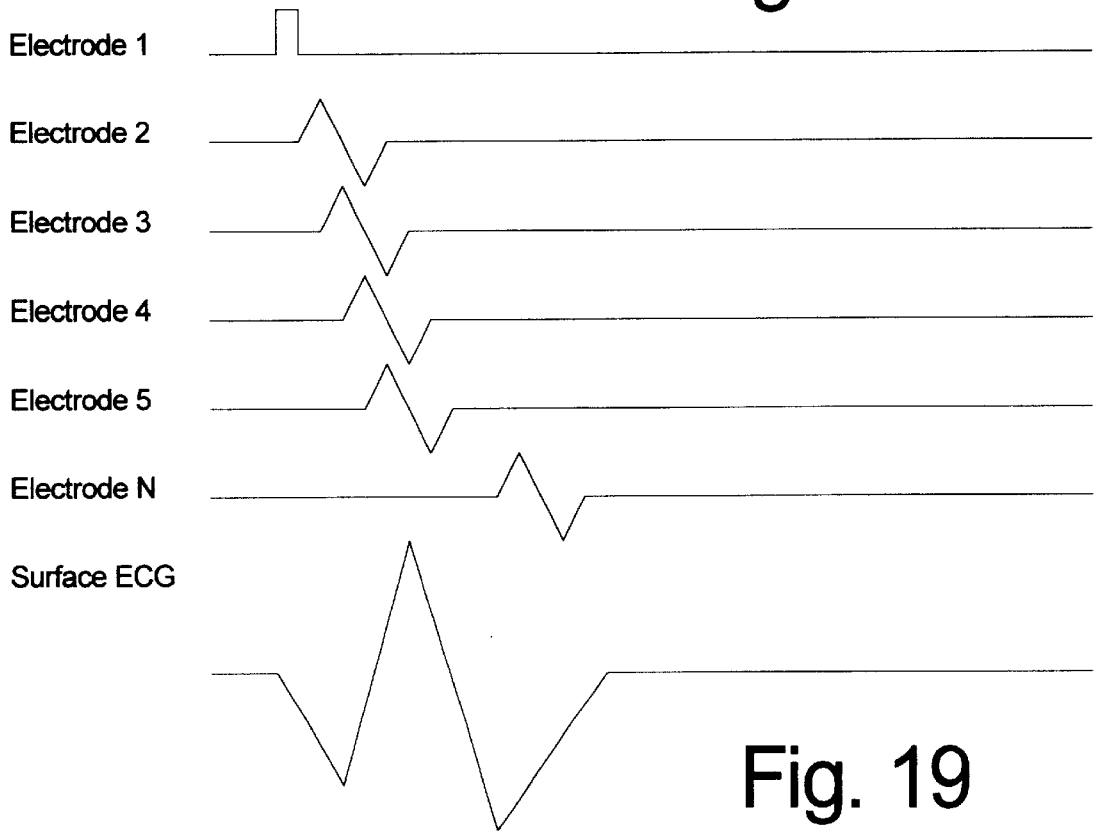
FIG. 19 is a graphical representation of a cardiac contraction caused by pacing at an optimal electrode as sensed by a plurality of electrodes and by an external ECG machine.

Sweet-spot pacing involves the determination of the optimal stimulating location within the heart chamber. As described above, the optimum electrode may be determined at the time of implantation. After implantation, similar search algorithms may be used either through the cardiac stimulator 12 or with the programmer 100 to confirm or modify the selection of the optimum electrode, as conditions change over time. Current pulse generators stimulate from an electro-physiologically arbitrary point determined by implant technique. Stimulation at a conventionally implanted electrode may produce a wave front similar to that illustrated in FIG. 18. Like the ectopic wave of FIG. 17, the wave front propagates across the heart in a less natural manner. Longer intervals between sensed events and an extended QRS signature may be due to the fact that the wave front follows cellular conduction rather than the faster Purkinje fibers. Where the optimum electrode has been identified, as described above, pacing at the optimum electrode may produce the more natural and efficient contraction illustrated in FIG. 19.

Figure 20:
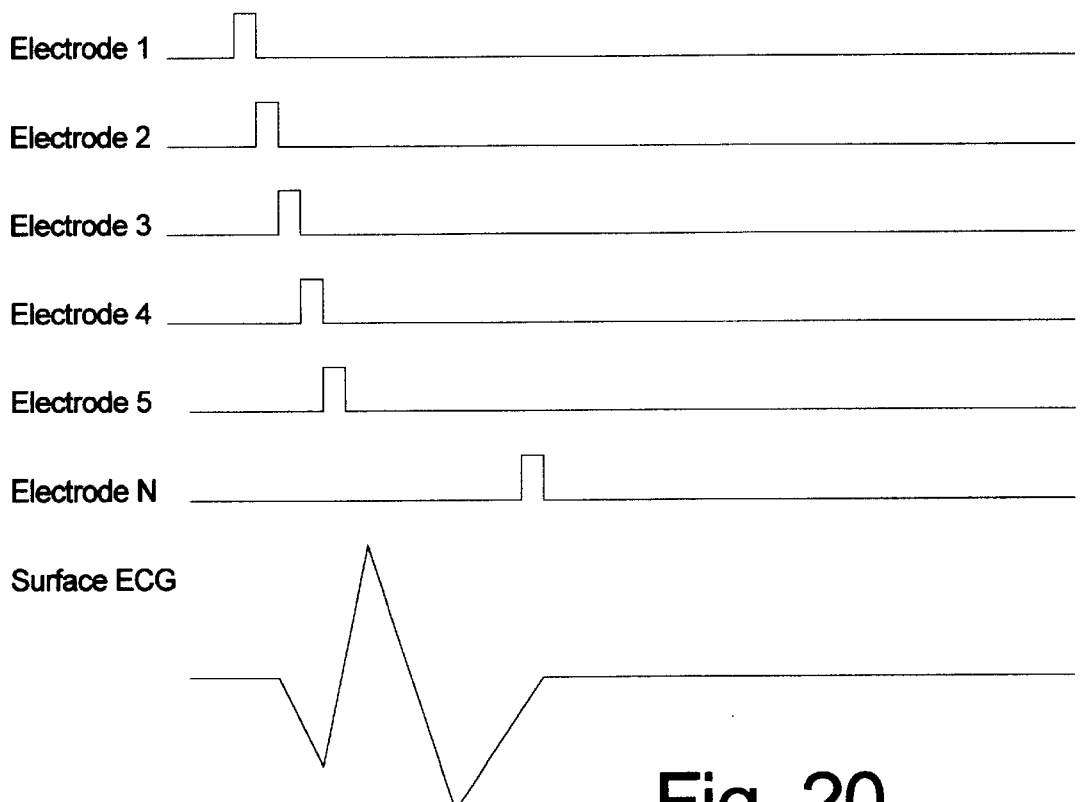
FIG. 20 is a graphical representation of a cardiac contraction caused by sequential pulse train pacing at a plurality of electrodes as sensed by a plurality of electrodes and by an external ECG machine.

In patients whose natural conduction system is insufficient, sequential pulse train pacing may be used to improve cardiac performance. This kind of pacing is illustrated in FIG. 20. Following the pattern of a normal wave front, FIG. 16, a train of pulses proceeds through the electrodes in an order and at time delays that track the path of the normal wave front. The contraction of the heart is rendered more efficient, allowing the heart to accomplish its task with less effort, thereby allowing the symptoms of Congestive heart failure to be alleviated. It is not always necessary to pace at each electrode in the series. Because the apparatus provides for sensing at each of the electrodes as well as pacing, the heart may be paced at a given electrode only if the wave front does not reach that electrode within the delay time set in the ordered pair associated with that electrode. As pointed out above, the ordered pairs may be adjusted by a physician to improve the efficiency of the contraction and set a desired template for the wave front. The apparatus would then stimulate the heart at one or more electrodes to bring the actual action of the heart into conformity with the template, as far as possible.

An important aspect of this invention comprises modifying the intrinsic ventricular cardiac activation sequence and generating simultaneous or near simultaneous pacing pulses to the septum or the right ventricular outflow tract during ventricular systole in order to improve left ventricular cardiac efficiency and reduce mitral regurgitation in patients with dilated cardiomyopathy. It is asserted that specialized stimulation from the right side of the heart can so improve left side performance that left ventricular output can be improved. Cardiac remodeling may also take place. One source of left ventricular inefficiency may be increased mitral valve regurgitation. A second source may be increased septal motion. In the weakened heart, the right and left ventricles may become dysynchronus. In the healthy heart, the septal wall remains relatively straight, balanced between pressures of the contracting right ventricle and the contracting left ventricle. In the ailing heart, the right ventricle may first push the septum into the left ventricle and the left ventricle, contracting later, may then push the septum back into the right ventricle. The septum oscillates back and forth and the energy of the heart is used up in this motion, rather than in pushing blood out of the heart and through the circulatory system. Both sources of left ventricular inefficiency may be treated by appropriate stimulation to contract or stiffen heart muscles. Stimulation through at least one and preferably two or more electrodes lying along the septal wall in the right ventricle may so stiffen the septum that flutter or oscillation is reduced and cardiac performance is improved. Similarly, stimulation through at least one electrode in or near the right ventricular outflow tract may propagate into the base of the left ventricle, stiffening the muscular structures around the mitral valve and increasing left ventricular output. Achieving these results requires selecting an electrode or set of electrodes from a set of electrodes located along the right ventricular septal wall and extending into the right ventricular outflow tract. Preferably the lead 14 is deployed in the right ventricle as shown in FIG. 11. Preferably sufficient electrodes are disposed along the septal wall a sufficient probability of stimulating the heart at an effective region within a selected period of time. The selected period of time is believed to be the first 20% of right ventricular contraction time, more preferably 10% or less of the right ventricular contraction time. The probability of stimulating at or near an ideal sport should be at least 25%, more preferably at least 50%, yet more preferably 100%. At least 3, more preferably 5, and yet more preferably 12, electrodes are disposed along the lead in the region of the septal wall.

The number of electrodes to be deployed for a given patient may be determined as follows. It will be recognized that any number of electrodes exceeding calculated number will meet the selected conditions of stimulation time and coverage probability. The conduction velocity of a contraction wave form through a ventricle is on the order of 500 mm/sec or 0.5 mm/ms. The ventricular contraction takes about 40 ms and it is desirable to have the septum rigid within the first 10% of the contraction time, or within 4 ms. At the given conduction velocity, the effects of stimulation from a given electrode would travel about 2 mm in 4 ms. For complete coverage, adjacent electrodes would be about 4 mm apart.

The distance d from the center of one electrode to the center of an adjacent electrode may be calculated as follows:

$$d = e + 2*cv*t*(100/c)$$

where e is the electrode length, cv is the conduction velocity, t is the maximum conduction time and c is the selected percent coverage. For example, if the electrode length is 2 mm, and 100% coverage is desired, the electrode center-to-center distance is 6 mm. The number of electrodes deployed along a septum 5 cm (50 mm) long would be twelve. If 50% coverage were desired, 5 electrodes must be deployed on the same septum. If 25% coverage is desired, 3 electrodes would be deployed on the 5 cm septum. The distance d is not necessarily the spacing of the electrodes along the lead 14, except in configurations such as shown in FIG. 9. In lead configurations such as FIG. 10, additional electrodes must be provided to increase the probability that electrodes that fall on the septal wall are separated by the desired distance d.

The number and spacing of electrodes on the septal wall may also be affected by the number (n) of desirable pacing locations on a particular patient's septal wall. One or more "sweet" spots may be located by selective stimulation as described herein. If there are more than one sweet spots, but only one of the spots needs to be stimulated within the desired time to achieve septal rigidity, the probability or likelihood (l) of stimulation is $$l = 1 - ((100-c)/100)^n$$

where c is the percent covered and n is the number of desired points or sweet spots. The likelihood of stimulation l is a number between 0 and 1. If more than one of the sweet spots needs to be stimulated to achieve septal rigidity, the likelihood l is $$l = (1 - ((100-c)/100)^n)^p$$

where p is the number of sweet spots that must be stimulated.

These equations may be reversed to determine the desired spacing of electrodes along the septal wall, which will aide the physician in selecting the appropriate multi-electrode lead and lead configuration. For example, if a particular patient is expected to have 5 sweet spots on the septal wall, 2 of which must be stimulated with a 75% certainty (l=0.75) to achieve septal rigidity, then coverage c is $$c = 1 - \sqrt[n]{1 - \sqrt[p]{l}}$$

Figure 22:
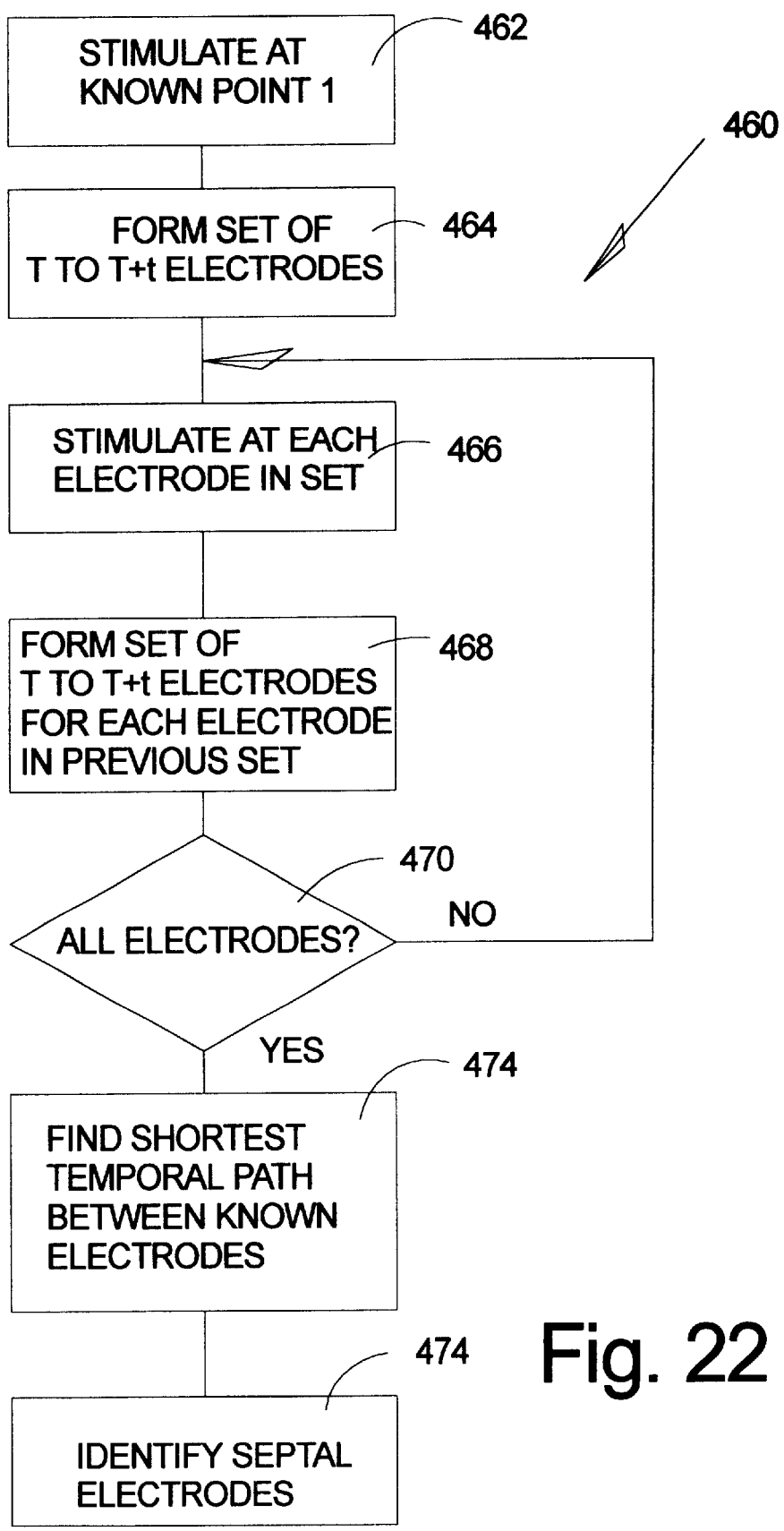
FIG. 22 is a flow chart of a program for identifying a set of electrodes on or near the right ventricular septal wall.
Figure 23:
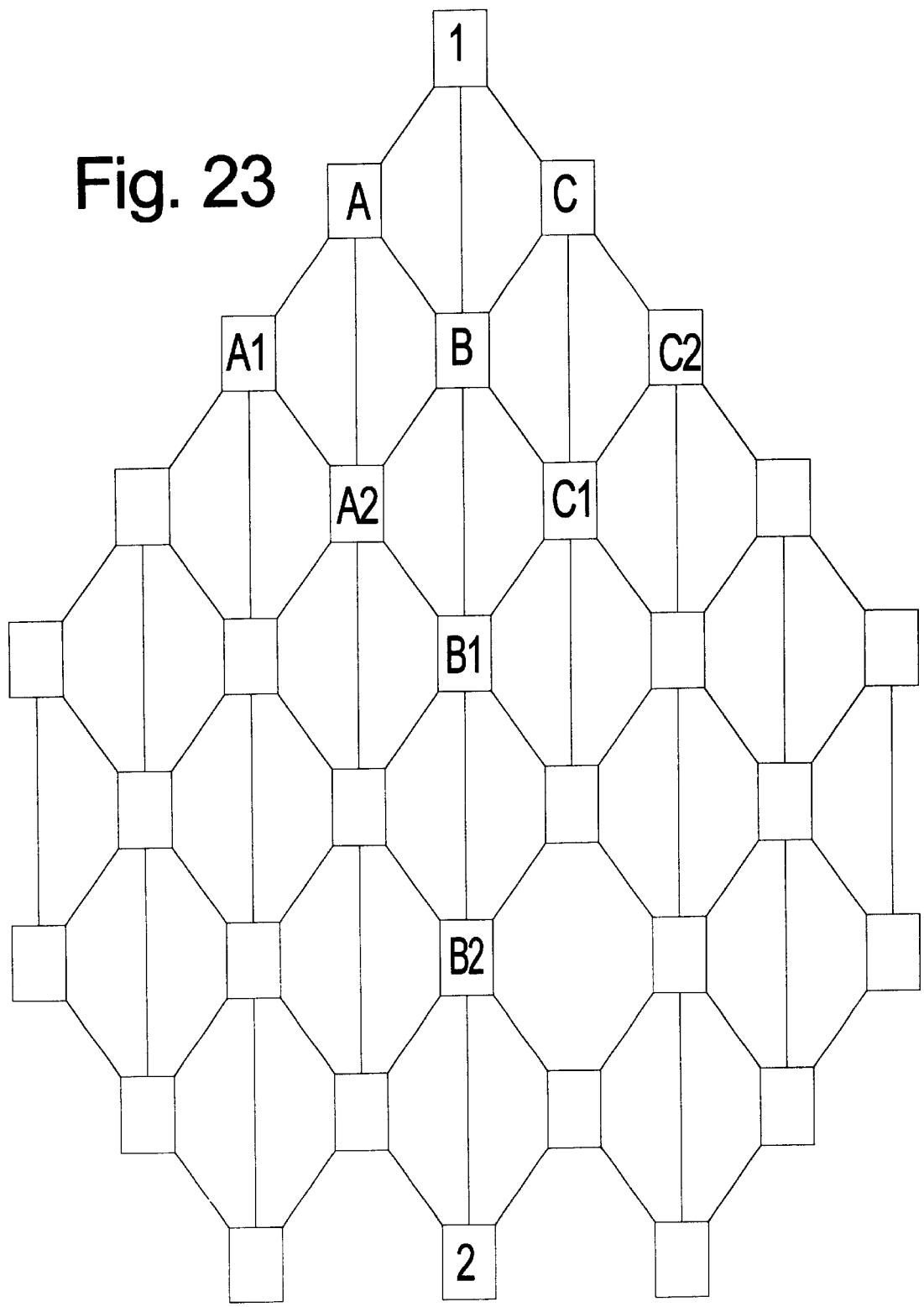
FIG. 23 is a graphical representation of electrodes selected in connection with the program of FIG. 22.

For the selected parameters this would be c=0.33 or 33%. The center-to-center distance would be 14 mm, or 4 electrodes for a 50 cm septal wall. The number of electrodes would be rounded up to the nearest whole number of electrodes.

Where multiple points are stimulated from multiple electrodes, the timing of stimulating pulses may be simultaneous or the pulses may be delivered at slightly varying times such that the wave fronts propagating from the electrodes arrive at their respective stimulation points at substantially simultaneous times.

Where the preferred configuration of the lead 14 shown in FIG. 9 or 11 is used, most of the electrodes will fall on or near the right ventricular septal wall or in the right ventricular outflow tract. In other lead configurations, such as FIG. 8 or 10, the step 412 of identifying electrodes near the septum or RV outflow tract may be more difficult. A line of electrodes lying on the septum may be selected where two electrodes on the septum are known. The most distal or tip electrode on the lead is usually secured to the heart near the right ventricular outflow tract or the septal wall near the base of the right ventricular chamber and its location is known by reason of fluoroscopic observation during implantation. A second electrode may be located by observation of a radio opaque marker proximally on the lead. An electrode near the radio opaque marker may be determined to lie sufficiently near the apex of the heart and close to the septal wall. Alternatively, a temporary lead may be inserted in the heart and a distal electrode advanced to the septal wall near the apex of the right ventricular chamber. A grid mapping of the electrodes may then be developed, as described below. The desired set of electrodes on the septal wall are those electrodes on the shortest path containing the two known electrodes. As shown in FIG. 22 a program 460 begins by stimulating 462 the heart at a known electrode, preferably the distal electrode on the lead 14. A set of adjacent electrodes 464 is identified, comprising the first electrode sensing the stimulating pulse and all electrodes sensing the pulse within a pre-selected time t thereafter. In FIG. 23, this set comprises electrodes A, B and C, adjacent electrode 1, which is the known distal electrode. The apparatus then stimulates the heart from each electrode in the set ABC, step 466 and forms (step 468) additional subsets, for example, A1, A2 and B from electrode A; A2, B1 and C1 from electrode B; and B, C1 and C2 from electrode C. Unless all electrodes have acted as a stimulating electrode (step 470), this process is repeated until a complete map ordering the electrodes has been developed, as suggested in FIG. 23. The electrodes on or near the septum will be selected (step 472) as those electrodes in the shortest temporal path from electrode 1 to the other known electrode, electrode 2, which may be an electrode on the lead 14 or an electrode on a temporary lead, as explained above. In FIG. 23, this set of septal electrodes would be electrodes 1, B, B1, and B2. Electrode 2 would be included if it is an electrode on the multi-electrode lead. If electrode 2 is on a temporary lead, it would not be included in the set of septal electrodes. The set of septal electrodes is then set 474 for use in identifying the optimum electrodes for stiffening the septum or the mitral valve, as explained above.

Figure 21:
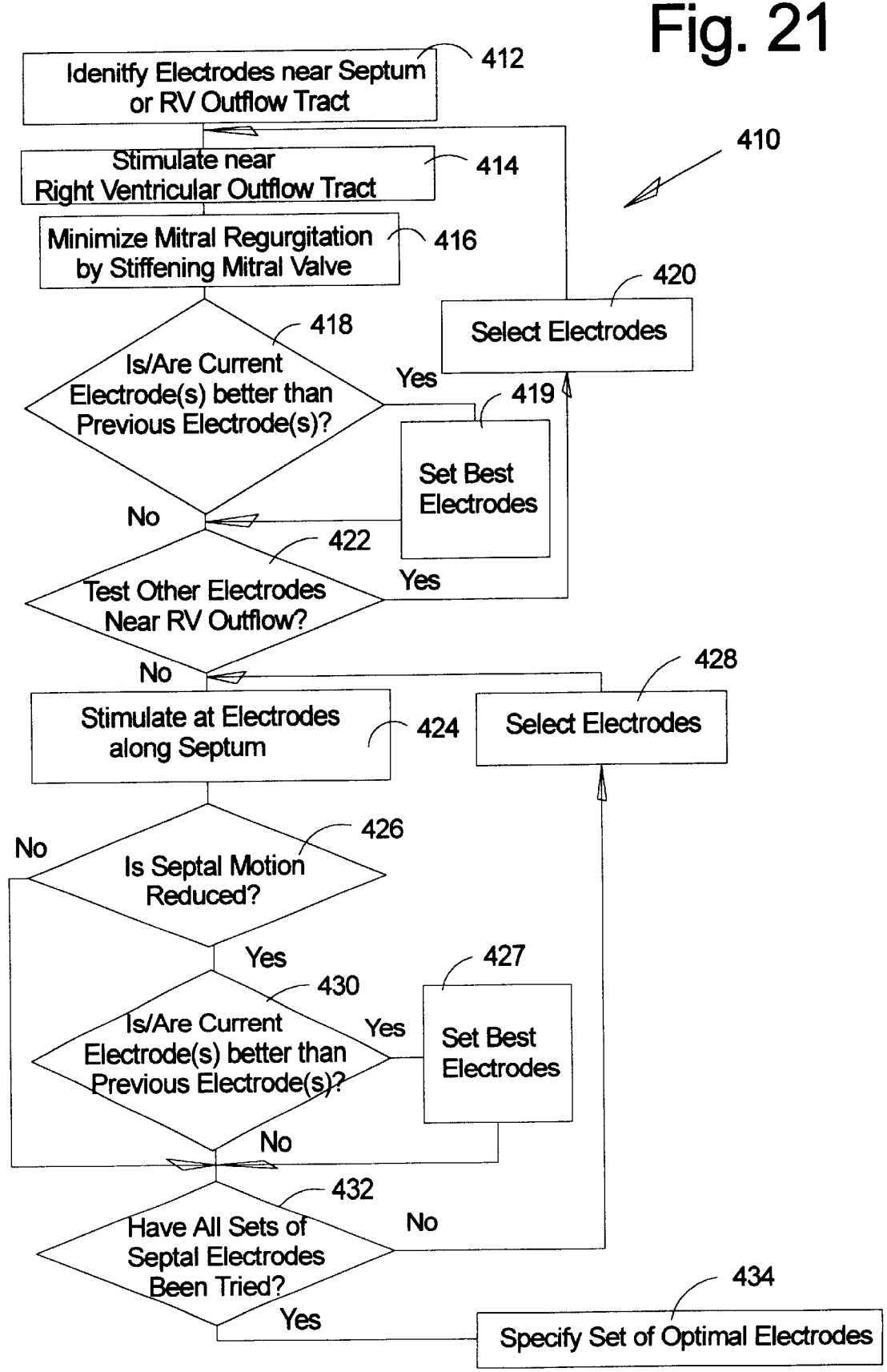
FIG. 21 is a flow chart of a program for providing a therapy for congestive heart failure.

FIG. 21 illustrates an algorithm 410 for providing a stimulation therapy for congestive heart failure by stimulation from the right ventricle and right ventricular outflow tract. First, a set of electrodes on the multi-electrode lead is identified 412. This set of electrodes lies on or near the right ventricular septal wall or in the right ventricular outflow tract. A first effort may be made to identify a subset of electrodes that stimulate the heart at locations such that the muscles around the mitral valve will stiffen and mitral regurgitation will be reduced. The heart is stimulated 414 through an electrode located near the right ventricular outflow tract. Data is acquired 416 indicative of the effectiveness of the stimulation in reducing mitral regurgitation. The cardiac imaging device 101 is usually employed. Data acquired by Doppler echocardiogram may indicate a reduced or eliminated backflow through the mitral valve. This data may be communicated across the link 105 to the programmer 100. Alternatively, an attending health care provider may observe the output of the cardiac imaging device 101 and enter a determination of the effect of a stimulus on mitral regurgitation into the programmer 100. The programmer 100 (or cardiac stimulator 12) compares 418 regurgitation information for the present stimulation electrode or electrodes with information from previous electrode or sets of electrodes. If no improvement is noted, the program inquires 422 if there is another electrode or set of electrodes in or near the right ventricular outflow tract that is a candidate for stimulation. If there is another electrode or set of electrodes, those electrodes are selected 420, and the heart is stimulated 414 again. If not, the program 410 will locate an electrode or set of electrodes that stiffen the septum in such a way that septal motion is reduced. If there is an improvement at step 418, the current set of electrodes is set as optimum 419 and the test for other candidate electrodes 420 is performed.

The program 410 begins its search by stimulating 424 the heart at an electrode or set of electrodes on or near the right ventricular septal wall. The program may serially select single electrodes, than sets of two electrodes, then sets of three electrodes, and so on until a sufficient number of combinations has been tried. Data is acquired to indicate if septal motion has been reduced 426 by the stimulation. This may be accomplished by digitizing features of the images captured by the cardiac imaging device 101 and transferring this information to the programmer 100 or cardiac stimulator 12. Alternatively, the attending health care provider may observe the output of the cardiac imaging device 101 and enter a determination of the effect of a stimulus on septal motion into the programmer 100. The programmer 100 (or cardiac stimulator 12) compares 430 septal wall motion information for the present stimulation electrode or electrodes with information from previous electrode or sets of electrodes. If no improvement is noted, and additional electrode candidates exist (step 432), then a new electrode or set of electrodes is selected 428 and the heart is stimulated again 424. If there is an improvement, program test if the current set of electrodes is better than the previous optimal set 430. If the new set is better than the previous optimal set, the new set is set as optimum 427, and the program inquires 432 if there is another electrode or set of electrodes in or near the right ventricular outflow tract that is a candidate for stimulation. If there is another electrode or set of electrodes, those electrodes are selected 428, and the heart is stimulated 424 again.

After both test sequences for mitral regurgitation and septal wall motion have been performed, a set of optimal electrodes is specified 434. For any given patient, of course, an attending physician may elect to treat only mitral regurgitation or ventricular wall motion without departing from the teachings of this invention. The set of optimal electrodes is identified in the cardiac stimulator 12 and used for stimulating the heart. In the treatment of congestive heart failure, it may be advantageous to stimulate the right ventricle slightly ahead of an expected physiologic contraction, thereby controlling the contraction of the heart from the optimal sites. Thus modern conventional pacers may sense cardiac events in the atrium and wait for a corresponding propagation of the event into the ventricle, stimulating the heart only if timely propagation fails to occur. To treat congestive heart failure, the cardiac stimulator may sense in the atrium, but stimulate in the ventricle at a time sooner than the expected propagation of the intrinsic wave into the ventricles. Alternatively, the ventricle may be stimulated at a rate slightly faster than the patient's expected heart rate. The expected heart rate may be estimated, may be determined by electrical sensing or may be determined by rate responsive sensing, such as by sensing an accelerometer. This anticipatory stimulation allows the cardiac stimulator 12 to control not only the timing of contraction, but also the shape of the contraction, including the preparatory stiffening of the septal wall or muscles around the mitral valve. The shaped contraction is believed to improve cardiac output, and in particular, to allow improved left ventricular performance from electrodes implanted in the right ventricle.

Figure 24:
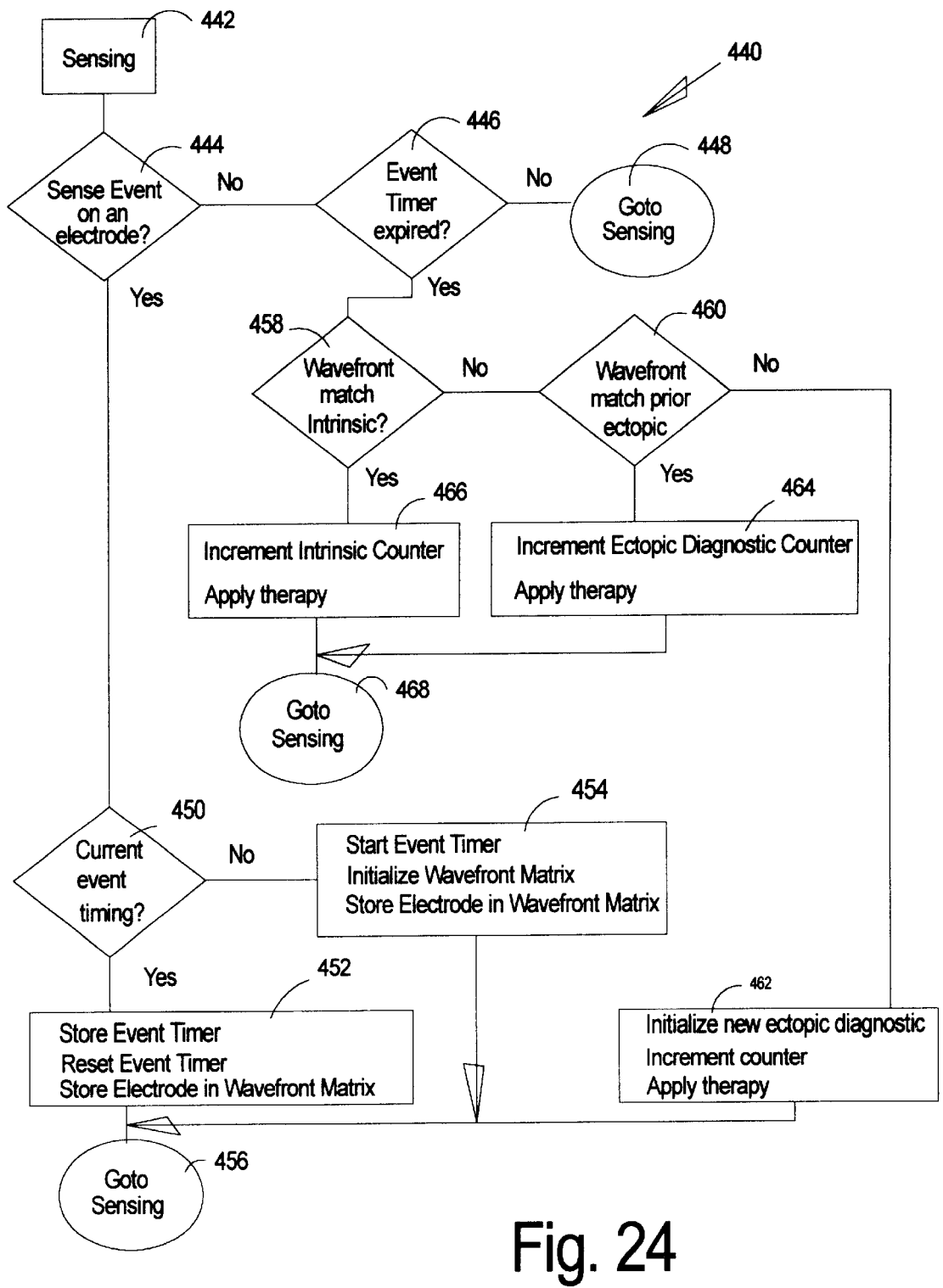
FIG. 24 is a flow chart of a program for gathering data concerning cardiac wave fronts and providing therapy.

The apparatus of the cardiac stimulator 12 and the multi-electrode lead 14 may also be adapted to perform the diagnostic and therapeutic functions as illustrated in the program 440 of FIG. 24. Sensing 442 through the multiple electrodes, as described above, monitors the heart for the occurrence of sense events. If an event is not detected (step 444), the apparatus checks for the expiration of an event timer 446. The event timer times various periods during a cardiac cycle. For example, a relatively long time may be set between the completion of one complete cardiac contraction and associated QRS complex, and the beginning of a second contraction. After an initial sense event (electrode 1 in FIG. 16) or an initial pace (electrode 1 in FIG. 19), shorter Delta Time periods from the ordered pairs defined above would be used. Thus the algorithm will follow the pattern set by a matrix of ordered pairs comprising electrodes and times and will try to create a more normal contraction wave front. If the event timer for the state has not expired, the apparatus will continue sensing 448. If an event is sensed on an appropriate electrode (step 444), the apparatus checks 450 if the event timer is running. If the timer is running, the elapsed time is stored, together with the identification of the sensing electrode, and the timer is reset 452. If the event timer is not running, the timer is started 454 and the wave front matrix is initialized. This would indicate the beginning of a new intrinsic cardiac contraction. The programming will follow the progress of the wave front and, if necessary, remodel the wave front to a more efficient form. The process begins by returning 456 to sensing 442.

When the cardiac contraction takes a longer, less efficient form, the event timer will expire at step 446 before the wave front is sensed at the next electrode in series. The program checks 458 if the wave front is following an intrinsic pattern, as explained above, that is that the wave front is proceeding generally from a focus through a chamber of the heart. If not, the wave front and contraction are considered ectopic, and the program compares the pattern to previously detected ectopic beats or contractions, for diagnostic purposes. If a new pattern is detected, a record is made of the form of the ectopic contraction, and therapy is applied 462. This may include stimulation at a particular electrode to drive the wave front back into a more efficient form. If the ectopic pattern has previously been recorded, a counter for that pattern is incremented and therapy is applied 464. On the other hand, if the wave front matches an intrinsic pattern (step 458), an intrinsic wave front counter is incremented and therapy applied 466 as above. After therapy in each of these three cases, the program returns 456, 468 to sensing 442.

Data acquired by the cardiac stimulator 12 on the frequency and form of ectopic and intrinsic wave fronts can be used to refine the form of therapy applied. The matrix of ordered pairs representing the desired wave front for an efficient contraction can be modified in response to the particular needs of a patient. The apparatus described herein allows for stimulation of the heart at a location likely to produce an efficient contraction and for subordinate stimulation to reshape a contraction waveform that has started spontaneously or from an initial stimulating pulse. Improved cardiac efficiency reduces the effects of congestive heart failure.

Numerous other modifications may be made to this invention without departing from its scope as defined in the attached claims.

What is claimed is:

1. A method for treating congestive heart failure comprising
    implanting a multi-electrode lead in at least the right ventricle of the heart of a patient, said multi-electrode lead having at least three selectable electrodes,
    implanting a cardiac stimulator in the body of said patient, said cardiac stimulator being connected to said multi-electrode lead,
    selecting a subset of said electrodes lying on the right septal wall for stimulating the heart such that stimulation through said set of electrodes improves cardiac performance, and
    stimulating the heart through said set of electrodes.

2. The method of claim 1 further comprising developing a plurality of template patterns of wave fronts passing said electrodes and distinguishing between intrinsic and ectopic wave fronts by comparing sensed wave fronts to said template patterns.

3. The method of claim 1 wherein the step of selecting said set of electrodes further comprises selecting a set of electrodes to stiffen the septum during systole.

4. The method of claim 1 wherein the step of selecting said set of electrodes comprises selecting a set of electrodes to reduce motion of the septum during systole.

5. The method of claim 4 wherein the motion of the septum is imaged.

6. The method of claim 3 wherein the septum is stimulated within at least the first 10 per cent of ventricular contraction time.

7. The method of claim 3 wherein the step of stimulating the heart comprises stimulating at said set of electrodes to stiffen the septum substantially simultaneously.

8. The method of claim 3 wherein the step of stimulating the heart comprises stimulating at said set of electrodes to stiffen the septum in a sequence such that substantially all of the septum stiffens substantially simultaneously.

9. The method of claim 1 wherein said multi-electrode lead is implanted from the right ventricular outflow tract along the right ventricular septal wall to the right ventricular apex.

10. The method of claim 1 wherein the set of electrodes lying on the septal wall is selected by identifying a set of electrodes close to a line connecting two electrodes that are known to lie on the septal wall.

11. The method of claim 1 wherein the step of selecting a set of electrodes further comprises selecting a set of electrodes near the right ventricular outflow tract.

12. The method of claim 11 wherein the step selecting said set of electrodes further comprises selecting a set of electrodes to stiffen the heart around the mitral valve during systole.

13. The method of claim 12 wherein the mitral regurgitation is minimized by stimulation from the right side of the heart.

14. The method of claim 13 wherein mitral regurgitation is imaged by an echo cardiogram.

15. The method of claim 1 wherein the step of implanting said multi-electrode lead comprises distributing sufficient electrodes on the right ventricular septal wall such that at least fifty per cent of the right ventricular wall could be stimulated within the first ten percent of the ventricular contraction time.

16. The method of claim 15 wherein said electrodes are within 8 mm of each other.

17. The method of claim 16 wherein the electrodes are within 4 mm of each other.

18. The method of claim 1 wherein the step of selecting a set of said electrodes comprises stimulating said heart to locate an electrode lying near a sweet spot in the heart.

19. The method of claim 18 further comprising stimulating at at least one electrode, sensing a physiologic parameter correlated to cardiac output, and selecting an electrode or electrodes such that said cardiac output is maximized.

20. The method of claim 1 wherein the step of selecting a set of electrodes comprises determining a three dimensional position for each electrode.

21. The method of claim 1 wherein the step of selecting a set of electrodes comprises mapping the progress of a wave front through at least a portion of the heart past at least some of said electrodes.

22. The method of claim 21 wherein said step of mapping a wave front comprises mapping an intrinsic contraction wave front.

23. The method of claim 21 wherein the step of mapping a wave front comprises stimulating the heart at at least one electrode and sensing a resulting wave front propagating through the heart.

24. The method of claim 1 wherein the step of stimulating the heart comprises sequentially stimulating at a plurality of electrodes.

25. The method of claim 24 wherein sequentially stimulating comprises stimulating at said electrodes to cause the contraction wave form to conform to a selected normal wave form.

26. A method for treating congestive heart failure comprising
implanting a multi-electrode lead in at least the right ventricle of the heart of a patient, said multi-electrode lead having at least three selectable electrodes,
implanting a cardiac stimulator in the body of said patient, said cardiac stimulator being connected to said multi-electrode lead,
developing a plurality of template patterns of wave fronts passing said electrodes;
distinguishing between intrinsic and ectopic wave fronts by comparing sensed wave fronts to said template patterns;
selecting a subset of said electrodes for stimulating the heart such that stimulation through said set of electrodes improves cardiac performance, and
stimulating the heart through said set of electrodes.

27. A method for treating congestive heart failure comprising
implanting a multi-electrode lead in at least the right ventricle of the heart of a patient, said multi-electrode lead having at least three selectable electrodes,
implanting a cardiac stimulator in the body of said patient, said cardiac stimulator being connected to said multi-electrode lead,
selecting a first subset of said electrodes near the right ventricular outflow tract;
stimulating the heart through said first subset of said electrodes;
determining a first regurgitation through the mitral valve;
selecting a second subset of said electrodes near the right ventricular outflow tract,
stimulating the heart through said second set of electrodes,
determining a second regurgitation through the mitral valve, and
choosing the subset of electrodes such that regurgitation through the mitral valve is minimized.

28. The method of claim 27 further comprising selecting additional subsets of said electrodes, determining regurgitation for each of said subsets and choosing an optimum subset from all of said subsets of electrodes.

29. A method for treating congestive heart failure comprising
implanting a multi-electrode lead in at least the right ventricle of the heart of a patient, said multi-electrode lead having at least three selectable electrodes,
implanting a cardiac stimulator in the body of said patient, said cardiac stimulator being connected to said multi-electrode lead,
selecting a subset of said electrodes lying on the right septal wall by
selecting a first electrode near the right ventricular outflow tract,
selecting a second electrode near the apex of the right ventricular chamber, and
identifying electrodes on the septal wall adjacent a shortest path connecting said first and second electrodes, and
stimulating the heart through said set of electrodes.

30. A method for treating congestive heart failure comprising
implanting a multi-electrode lead in at least the right ventricle of the heart of a patient, said multi-electrode lead having at least three selectable electrodes,
implanting a cardiac stimulator in the body of said patient, said cardiac stimulator being connected to said multi-electrode lead,
mapping the progress of a wave front past said electrodes;
selecting a subset of said electrodes for stimulating the heart in a sequence such that recreates the progress of said mapped wave front, and
stimulating the heart through said set of electrodes in said sequence.

31. The method of claim 30 wherein said step of stimulating the heart through said set of electrodes further comprises inhibiting stimulation at any individual electrode whenever an advancing wave front recreates said mapped wave front at said individual electrode.

32. The method of claim 30 wherein said step of mapping the progress of said wave front comprises mapping an intrinsic contraction wave front.

* * * * *